United States Patent
Nowruzi et al.

(10) Patent No.: US 11,696,967 B2
(45) Date of Patent: *Jul. 11, 2023

(54) APPARATUS AND METHOD FOR STERILIZING ENDOSCOPE

(71) Applicant: ASP Global Manufacturing GmbH, Schaffhausen (CH)

(72) Inventors: Keyvan Nowruzi, Mission Viejo, CA (US); Navid Omidbakhsh, Mission Viejo, CA (US)

(73) Assignee: ASP Global Manufacturing GMBH

( * ) Notice: Subject to any disclaimer, the term of this patent is extended or adjusted under 35 U.S.C. 154(b) by 430 days.

This patent is subject to a terminal disclaimer.

(21) Appl. No.: 16/843,366

(22) Filed: Apr. 8, 2020

(65) Prior Publication Data
US 2020/0230279 A1    Jul. 23, 2020

Related U.S. Application Data

(63) Continuation-in-part of application No. 16/225,035, filed on Dec. 19, 2018, which is a continuation of
(Continued)

(51) Int. Cl.
*A61L 2/24* (2006.01)
*A61L 2/18* (2006.01)
(Continued)

(52) U.S. Cl.
CPC ...... *A61L 2/24* (2013.01); *A61L 2/14* (2013.01); *A61L 2/186* (2013.01); *A61L 2/20* (2013.01);
(Continued)

(58) Field of Classification Search
CPC ... A61L 2/24; A61L 2/14; A61L 2/186; A61L 2/20; A61L 2/202; A61L 2/208;
(Continued)

(56) References Cited

U.S. PATENT DOCUMENTS

| | | |
|---|---|---|
| 5,527,508 A | 6/1996 | Childers et al. |
| 5,645,796 A | 7/1997 | Caputo |

(Continued)

FOREIGN PATENT DOCUMENTS

| | | |
|---|---|---|
| CN | 1989893 A | 7/2007 |
| CN | 101065155 A | 10/2007 |

(Continued)

OTHER PUBLICATIONS

Japanese Notification of Reasons for Refusal dated Feb. 24, 2021, for Application No. 2017-127176, 7 pages.

(Continued)

*Primary Examiner* — Regina M Yoo
(74) *Attorney, Agent, or Firm* — Lerner David LLP

(57) ABSTRACT

A method of sterilizing an article includes receiving the article in a sterilization chamber. The method also includes applying a vacuum to a first pressure less than 100 torr. The method also includes introducing a sterilant into the sterilization chamber. The method also includes maintaining the first pressure in the sterilization chamber for a first period of time. The method also includes venting the sterilization chamber to a second pressure less than 100 torr. The method also includes maintaining the second pressure. The method also includes venting the sterilization chamber to a third pressure. The method also includes maintaining the third pressure. The method also includes venting the sterilization chamber to atmospheric pressure. The method further includes between venting and maintaining steps applying a vacuum to a fourth pressure less than 100 torr, introducing additional sterilant, and maintaining the fourth pressure.

21 Claims, 14 Drawing Sheets

Related U.S. Application Data application No. 15/198,670, filed on Jun. 30, 2016, now Pat. No. 10,314,929.

(51) Int. Cl.
*A61L 2/28* (2006.01)
*A61L 2/14* (2006.01)
*A61L 2/20* (2006.01)

(52) U.S. Cl.
CPC ............... *A61L 2/202* (2013.01); *A61L 2/208* (2013.01); *A61L 2/28* (2013.01); *A61L 2202/11* (2013.01); *A61L 2202/122* (2013.01); *A61L 2202/14* (2013.01); *A61L 2202/18* (2013.01); *A61L 2202/24* (2013.01)

(58) Field of Classification Search
CPC .. A61L 2/28; A61L 2202/11; A61L 2202/122; A61L 2202/14; A61L 2202/18; A61L 2202/24; A61L 2/18
See application file for complete search history.

(56) References Cited

U.S. PATENT DOCUMENTS

| | | | |
|---|---|---|---|
| 6,030,579 | A | 2/2000 | Addy et al. |
| 6,325,972 | B1 | 12/2001 | Jacobs et al. |
| 6,365,102 | B1 | 4/2002 | Wu et al. |
| 6,447,719 | B1 | 9/2002 | Agamohamadi et al. |
| 6,656,426 | B1 | 12/2003 | Wang et al. |
| 6,852,277 | B2 | 2/2005 | Platt et al. |
| 6,852,279 | B2 | 2/2005 | Williams et al. |
| 6,939,519 | B2 | 9/2005 | Agamohamadi et al. |
| 8,012,415 | B2 | 9/2011 | Hanada et al. |
| 8,230,616 | B2 | 7/2012 | McLaren et al. |
| 8,366,995 | B2 | 2/2013 | McLaren et al. |
| 8,882,680 | B2 | 11/2014 | Furlong et al. |
| 9,302,021 | B2 | 4/2016 | Klobusnik |
| 10,314,929 | B2 | 6/2019 | Nowruzi et al. |
| 2006/0280646 | A1 | 12/2006 | Shiosawa |
| 2008/0233002 | A1* | 9/2008 | Mizuno .................. A61L 2/202 422/22 |
| 2011/0076192 | A1 | 3/2011 | Robitaille et al. |
| 2011/0176959 | A1 | 7/2011 | Ko |
| 2013/0236355 | A1 | 9/2013 | Dufresne et al. |
| 2014/0037495 | A1 | 2/2014 | Ahishka et al. |
| 2015/0064067 | A1 | 3/2015 | Klobusnik et al. |
| 2017/0304477 | A1* | 10/2017 | Truong ..................... A61L 2/00 |
| 2018/0000976 | A1 | 1/2018 | Nowruzi et al. |
| 2019/0224356 | A1 | 7/2019 | Nowruzi et al. |

FOREIGN PATENT DOCUMENTS

| | | |
|---|---|---|
| CN | 103118581 A | 5/2013 |
| CN | 103747808 A | 4/2014 |
| CN | 104735893 A | 6/2015 |
| CN | 105407928 A | 3/2016 |
| CN | 105709249 A | 6/2016 |
| EP | 1455843 B1 | 8/2005 |
| EP | 3041519 B1 | 5/2021 |
| JP | H11-193010 A | 7/1999 |
| JP | 2015-223455 A | 12/2015 |
| WO | WO-2007080907 | 7/2007 |

OTHER PUBLICATIONS

Chinese Office Action and Search Report dated Jun. 3, 2020 for Application No. 201710526246.6, 14 pages.
European Search Report and Written Opinion dated Nov. 6, 2017 for Application No. 17178746, 8 pages.
U.S. Appl. No. 62/316,722, filed Apr. 1, 2016.
Partial International Search Report and Written Opinion dated Sep. 15, 2021, for International Application No. PCT/IB2021/000227, 17 pages.

* cited by examiner

APPARATUS AND METHOD FOR STERILIZING ENDOSCOPE

PRIORITY

This application is a continuation-in-part of U.S. patent application Ser. No. 16/225,035 entitled "Apparatus and Method for Sterilizing Endoscope," filed on Dec. 19, 2018, now published as U.S. Pat. Pub. No. 2019/0224356 on Jul. 25, 2019, which is a continuation of U.S. patent application Ser. No. 15/198,670 entitled "Apparatus and Method for Sterilizing Endoscope," filed on Jun. 30, 2016, now issued as U.S. Pat. No. 10,314,929 on Jun. 11, 2019, the disclosures of which are incorporated by reference herein.

BACKGROUND

Re-usable medical devices such as certain surgical instruments, endoscopes, etc., may be sterilized before re-use in order to minimize the likelihood that a contaminated device might be used on a patient, which could cause an infection in the patient. Various sterilization techniques may be employed, such as steam, hydrogen peroxide, peracetic acid, and vapor phase sterilization, either with or without a gas plasma and ethylene oxide (EtO). Each of these methods may depend to a certain extent on the diffusion rates of the sterilization fluids (e.g., gases) upon or into the medical devices to be sterilized.

Before sterilization, medical devices may be packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device. Diffusion of the sterilant may be particularly problematic for medical devices that have diffusion-restricted spaces therein because these diffusion-restricted spaces may reduce the likelihood that a sterilization cycle may be effective. For example, some endoscopes have one or more long narrow lumens into which the sterilant must diffuse in sufficient concentration for sufficient time to achieve a successful sterilization cycle.

Sterilization of medical devices may be performed with an automated sterilization system such as a STERRAD® System by Advanced Sterilization Products of Irvine, Calif. Examples of automated sterilization systems are described in U.S. Pat. No. 6,939,519, entitled "Power System for Sterilization Systems Employing Low Frequency Plasma," issued Sep. 6, 2005, the disclosure of which is incorporated by reference herein; U.S. Pat. No. 6,852,279, entitled "Sterilization with Temperature-Controlled Diffusion Path," issued Feb. 8, 2005, the disclosure of which is incorporated by reference herein; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein; U.S. Pat. No. 6,447,719, entitled "Power System for Sterilization Systems Employing Low Frequency Plasma," issued Sep. 10, 2002, the disclosure of which is incorporated by reference herein; and U.S. Provisional Pat. App. No. 62/316,722, entitled "System and Method for Sterilizing Medical Devices," filed Apr. 1, 2016, the disclosure of which is incorporated by reference herein.

Some sterilization systems may use vaporized chemical sterilants or chemical gas such as hydrogen peroxide, peracetic acid, ozone, chlorine dioxide, nitrogen dioxide, etc., to sterilize medical devices. Examples of such systems are described in U.S. Pat. No. 6,365,102, entitled "Method of Enhanced Sterilization with Improved Material Compatibility," issued Apr. 2, 2002, the disclosure of which is incorporated by reference herein, and U.S. Pat. No. 6,325,972, entitled "Apparatus and Process for Concentrating a Liquid Sterilant and Sterilizing Articles Therewith," issued Dec. 4, 2001, the disclosure of which is incorporated by reference herein. Some such systems provide a hydrogen peroxide/gas plasma sterilization system comprising a vacuum chamber and plasma source and increased concentration of hydrogen peroxide for sterilization. Some such systems may have difficulty sterilizing lumens of some medical devices if their length exceeds a certain value; or the processing time of such systems may still not be fast enough for some applications. Thus, some medical devices such as long and/or narrow flexible endoscopes may not be completely sterilized by these systems due to the insufficient reach of sterilant vapor to the inside of the channels. Such medical devices might therefore only be disinfected without being sterilized. Sterilization systems that use ethylene oxide may have a relatively long processing time (e.g., longer than 24 hours), which may be undesirable in some cases.

Operator error may result in medical devices that are erroneously believed to be decontaminated being returned to service. Confirming that a sterilization cycle has been efficacious may help medical personnel avoid using a contaminated medical device on a patient. The sterilized medical device might not itself be checked for contaminating organisms because such an activity may introduce other contaminating organisms to the medical device, thereby re-contaminating it. Thus, an indirect check may be performed using a sterilization indicator. A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms may be placed into a sterilization chamber alongside a medical device and subject to a sterilization cycle. After the cycle is complete, the microorganisms in the biological indicator may be cultured to determine whether any of the microorganisms survived the cycle. The presence or absence of living microorganisms in the biological indicator will indicate whether the sterilization cycle was effective.

While a variety of systems and methods have been made and used for surgical instrument sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Sterilization System

Figure 1:
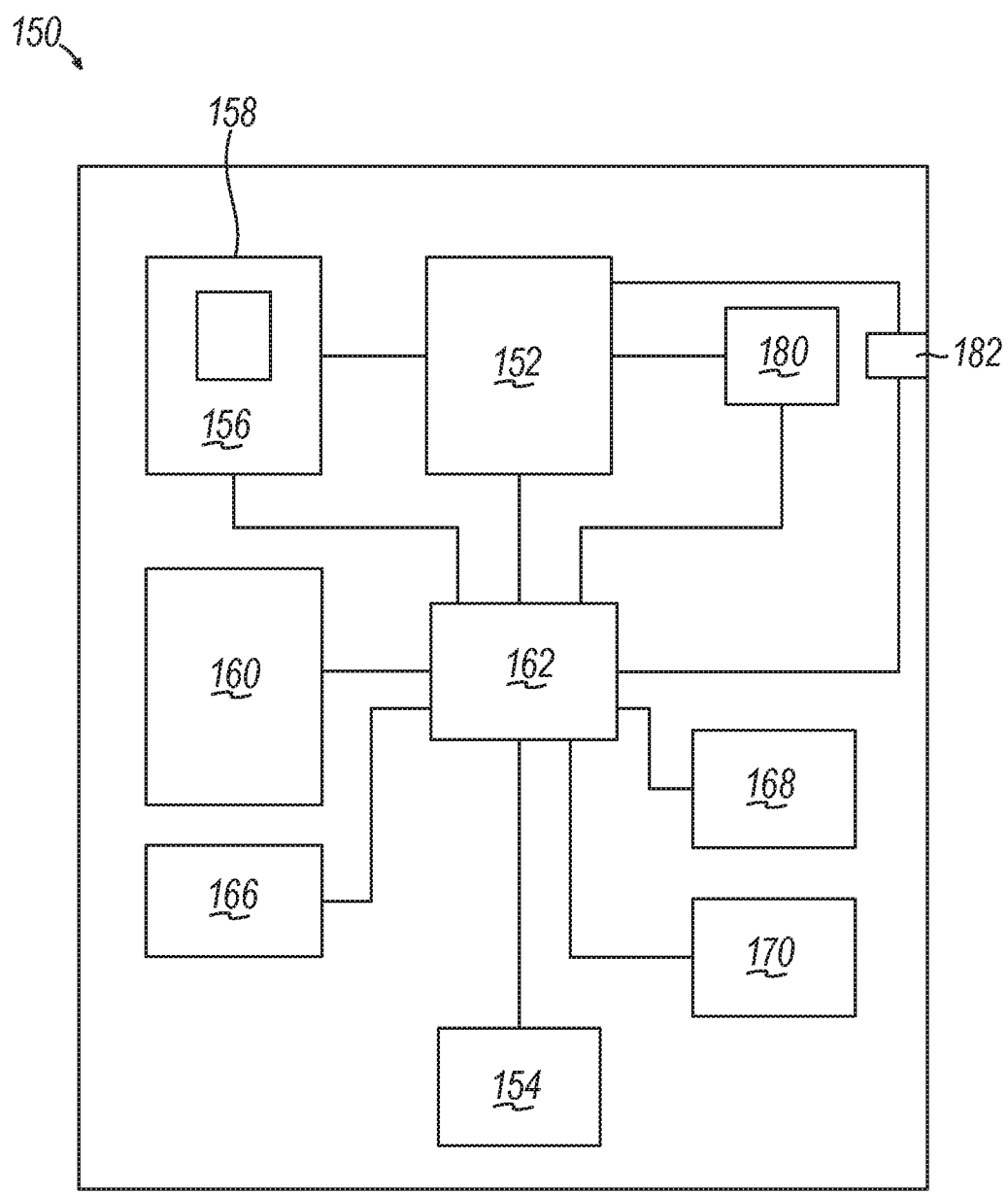
FIG. 1 depicts a schematic view of an exemplary medical device sterilizing cabinet.

FIG. 1 depicts an exemplary sterilizing cabinet (150) that is operable to sterilize medical devices such as endoscopes, etc. Sterilizing cabinet (150) of the present example includes a sterilization chamber (152), which is configured to receive one or more medical devices for sterilization. While not shown, sterilizing cabinet (150) also includes a door that opens and closes sterilization chamber (152) in response to actuation of a kick plate. An operator may thereby open and close sterilization chamber (152) in a hands-free fashion. Of course, any other suitable features may be used to provide selective access to sterilization chamber. Sterilizing cabinet (150) also includes a sterilization module (156) that is operable to dispense a sterilant into sterilization chamber (152) in order to sterilize medical devices contained in sterilization chamber (152). In the present example, sterilization module (156) is configured to receive replaceable sterilant cartridges (158) containing a certain amount of sterilant. By way of example only, each sterilant cartridge (158) may contain enough sterilant to perform five sterilization procedures.

Sterilizing cabinet (150) of the present example further includes a touch screen display (160). Touch screen display (160) is operable to render the various user interface display screens, such as those described in U.S. Provisional Pat. App. No. 62/316,722, the disclosure of which is incorporated by reference herein. Of course, touch screen display (160) may display various other screens as well. Touch screen display (160) is further configured to receive user input in the form of the user contacting touch screen display (160) in accordance with conventional touch screen technology. In addition, or in the alternative, sterilizing cabinet (150) may include various other kinds of user input features, including but not limited to buttons, keypads, keyboards, a mouse, a trackball, etc.

Sterilizing cabinet (150) of the present example further includes a processor (162), which is in communication with sterilization module (156) and with touch screen display (160). Processor (162) is operable to execute control algorithms to drive sterilization module (156) in accordance with user input. Processor (162) is further operable to execute instructions to display the various screens on touch screen display (160); and to process instructions received from a user via touch screen display (160) (and/or via other user input features). Processor (162) is also in communication with various other components of sterilization cabinet (150) and is thereby operable to drive those components and/or process input and/or other data from those components. Various suitable components and configurations that may be used to form processor (162) will be apparent to those of ordinary skill in the art in view of the teachings herein.

Sterilizing cabinet (150) of the present example further includes an identification tag reader (166), which is operable to read an identification tag of a biological indicator as described herein. By way of example only, identification tag reader (166) may comprise an optical reader that is operable to read an optical identification tag (e.g., barcode, QR code, etc.) of a biological indicator. In addition, or in the alternative, identification tag reader (166) may comprise RFID reader that is operable to read an RFID identification tag (e.g., barcode, QR code, etc.) of a biological indicator. Various suitable components and configurations that may be used to form identification tag reader (166) will be apparent to those of ordinary skill in the art in view of the teachings herein. Data received through identification tag reader (166) is processed through processor (162).

Sterilizing cabinet (150) of the present example further includes a memory (168), which is operable to store control logic and instructions and that are executed by processor (162) to drive components such as sterilization module (156), touch screen display (160), communication module (154), and identification tag reader (166). Memory (168) may also be used to store results associated with setup of a sterilization cycle, performance of a load conditioning cycle, performance of a sterilization cycle, and/or various other kinds of information. Various suitable forms that memory (168) may take, as well as various ways in which memory (168) may be used, will be apparent to those of ordinary skill in the art in view of the teachings herein.

Sterilizing cabinet (150) of the present example further includes a printer (170), which is operable to print information such as results associated with setup of a sterilization cycle, performance of a load conditioning cycle, performance of a sterilization cycle, and/or various other kinds of information. By way of example only, printer (170) may comprise a thermal printer, though of course any other suitable kind of printer may be used. Various suitable forms that printer (170) may take, as well as various ways in which printer (170) may be used, will be apparent to those of ordinary skill in the art in view of the teachings herein. It should also be understood that printer (170) is merely optional and may be omitted in some versions.

Sterilizing cabinet (150) of the present example further includes a vacuum source (180) and a venting valve (182). Vacuum source (180) is in fluid communication with sterilization chamber (152) and is also in communication with processor (162). Thus, processor (162) is operable to selectively activate vacuum source (180) in accordance with one or more control algorithms. When vacuum source (180) is activated, vacuum source (180) is operable to reduce the pressure within sterilization chamber (152) as will be described in greater detail below. Venting valve (182) is also in fluid communication with sterilization chamber (152). In addition, venting valve (182) is in communication with processor (162) such that processor (162) is operable to selectively activate venting valve (182) in accordance with one or more control algorithms. When venting valve (182) is activated, venting valve (182) is operable to vent sterilization chamber (152) to atmosphere as will be described in greater detail below. Various suitable components that may be used to provide vacuum source (180) and venting valve (182) will be apparent to those of ordinary skill in the art in view of the teachings herein.

In addition to the foregoing, sterilizing cabinet (150) may be configured and operable in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; U.S. Pat. No. 6,447,719, the disclosure of which is incorporated by reference herein; U.S. Pat. No. 6,365,102, the disclosure of which is incorporated by reference herein; U.S. Pat. No. 6,325,972, the disclosure of which is incorporated by reference herein; and/or U.S. Provisional Patent App. No. 62/316,722, the disclosure of which is incorporated by reference herein.

II. Overview of Exemplary Sterilization Method

Figure 2:
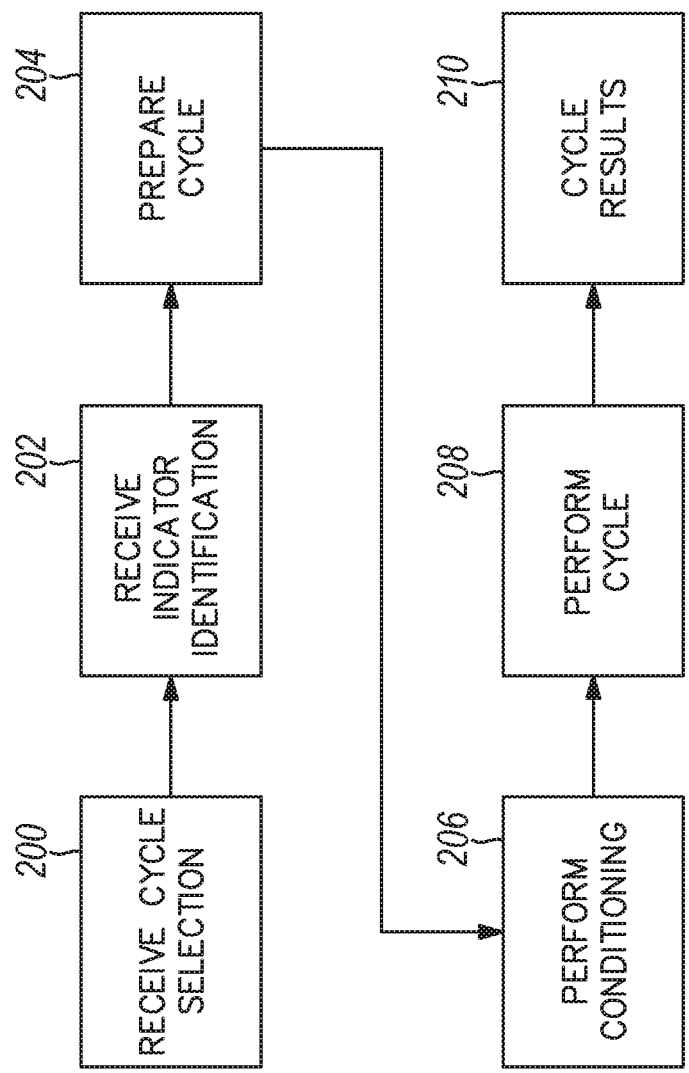
FIG. 2 depicts a high-level flowchart of an exemplary set of steps that a sterilizing cabinet of the system of FIG. 1 could perform to sterilize a medical device.

FIG. 2 depicts a high-level flowchart of an exemplary set of steps that sterilizing cabinet (150) could perform to sterilize a used medical device, such as an endoscope. Sterilizing cabinet (150) may be configured to perform one or more sterilization cycles, with different sterilization cycles being appropriate for different types and quantities of medical devices. Thus, as an initial step, sterilizing cabinet (150) may display one or more available sterilization cycles via touch screen display (160) and then receive a sterilization cycle selection (block 200) from the user.

Sterilizing cabinet (150) may also display instructions indicating whether a biological indicator should be used with the selected sterilization cycle, and receive a biological indicator identification (block 202). Such a biological indicator identification (block 202) may be provided via identification tag reader (166), via touch screen display (160), or otherwise. A biological indicator may be placed inside sterilization chamber (152) of sterilizing cabinet (150) before the sterilization cycle begins and may remain in the sterilization chamber during the sterilization cycle. The user may thus identify the particular biological indicator (block 202) before the biological indicator is placed in the sterilization chamber. The biological indicator may contain microorganisms that are responsive to a particular sterilization cycle. Upon completion of the sterilization cycle, the biological indicator may be tested for the microorganisms in order to provide a measure of the effectiveness of the sterilization cycle. A biological indicator may not necessarily be required for all sterilization cycles, but a biological indicator may be required based on hospital rules or local regulations.

Selection of a sterilization cycle (block 200) and identification of a biological indicator (block 202) may define one or more requirements for the configuration and arrangement of medical devices within sterilization chamber (152). Thus, in order to provide preparation for the sterilization cycle (204) once the sterilization cycle has been selected (block 200) and the biological indicator has been identified (block 202), sterilizing cabinet (150) may provide a display via touch screen display (160) indicating a proper medical device placement. This display may serve as a visual guide to a user's placement of medical device(s) (and perhaps a biological indicator) within sterilizing chamber (152) of sterilizing cabinet (150), based on the sterilization cycle selection (block 200). A door of sterilization chamber (152) may be opened to enable the user to place the medical device(s) (and perhaps a biological indicator) within sterilizing chamber (152) as instructed.

Once the user has placed the medical device in sterilizing chamber (152) based on these instructions, the user may press a start button or other button indicating that medical device placement is complete. In some versions, sterilizing cabinet (150) is configured to automatically verify proper medical device placement. By way of example only, sterilizing cabinet (150) may employ photo sensors, imaging devices, weight sensors, and/or other components to verify proper medical device placement in sterilizing chamber (152). It should be understood, however, that some versions of sterilizing cabinet (150) may lack the capability of automatically verifying proper placement of a medical device within sterilizing chamber (152).

If medical device placement is verified and/or the user has otherwise completed the cycle preparation (block 204), sterilizing cabinet (150) may start a load conditioning process (block 206). The load conditioning process (block 206) prepares sterilization chamber (152) and the medical device(s) within sterilization chamber (152) for optimal sterilization during a sterilization cycle. Conditioning may include controlling and optimizing one or more characteristics of sterilization chamber (152). For example, during load conditioning, sterilizing cabinet (150) may continuously monitor the level of moisture within sterilization chamber (152) while reducing the level of moisture by, for example, circulating and dehumidifying the air of sterilization chamber (152), creating a vacuum within sterilization chamber (152), heating sterilization chamber (152), and/or other methods for dehumidifying a sealed chamber. This may continue until sterilizing cabinet (150) determines that an acceptable level of moisture has been reached.

As part of the load conditioning cycle (block 206), sterilizing cabinet (150) may also continuously detect the temperature within sterilization chamber (152) while heating sterilization chamber (152) by, for example, convection of heated air, conduction through an interior surface of sterilization chamber (152), and/or using other techniques. This may continue until sterilizing cabinet (150) determines that an acceptable internal temperature has been reached. Various conditioning actions such as controlling temperature or humidity may be performed in parallel or in sequence. It should also be understood that the load conditioning cycle (block 206) may verify that the sterilization chamber is sealed; verifying contents of the sterilization chamber; checking physical characteristics of the contents of the sterilization chamber such as content volume, content weight, or other characteristics; and/or performing one or more conditioning steps that may include chemical treatment, plasma treatment, or other types of treatment to reduce moisture, raise temperature, and/or otherwise prepare the medical devices in sterilization chamber (152) for the sterilization cycle (block 208).

While the one or more conditioning actions are being performed as part of the load conditioning cycle (block 206), sterilizing cabinet (150) may display information via touch screen display (160) indicating to a user the duration of time before the sterilization cycle (block 208) performance may begin. Once all load conditioning criteria have been successfully met, the load conditioning cycle (block 206) is complete, and the sterilization cycle (block 208) may then be performed. It should therefore be understood that sterilizing cabinet (150) is configured such that the sterilization cycle (block 208) is not actually initiated until after the load conditioning cycle (block 206) is complete. It should also be understood that the load conditioning cycle (block 206) may be omitted or varied in some versions of sterilizing cabinet (150) operation.

As noted above, sterilization cabinet (150) may begin performing the sterilization cycle (block 208) automatically and immediately after load conditioning (block 206) has been completed. The sterilization cycle (block 208) may include exposing the medical device(s) in the sterilizing chamber to pressurized sterilant gas, further heat treatment, chemical treatment, plasma treatment, vacuum treatment, and/or other types of sterilization procedures. During performance of the sterilization cycle (block 208), sterilization cabinet (150) may display information via touch screen display (160) such as a duration remaining for the sterilization cycle (block 208), the current stage of the sterilization cycle (block 208) (e.g. plasma, vacuum, injection, heat, chemical treatment), and/or other information.

Figure 3:
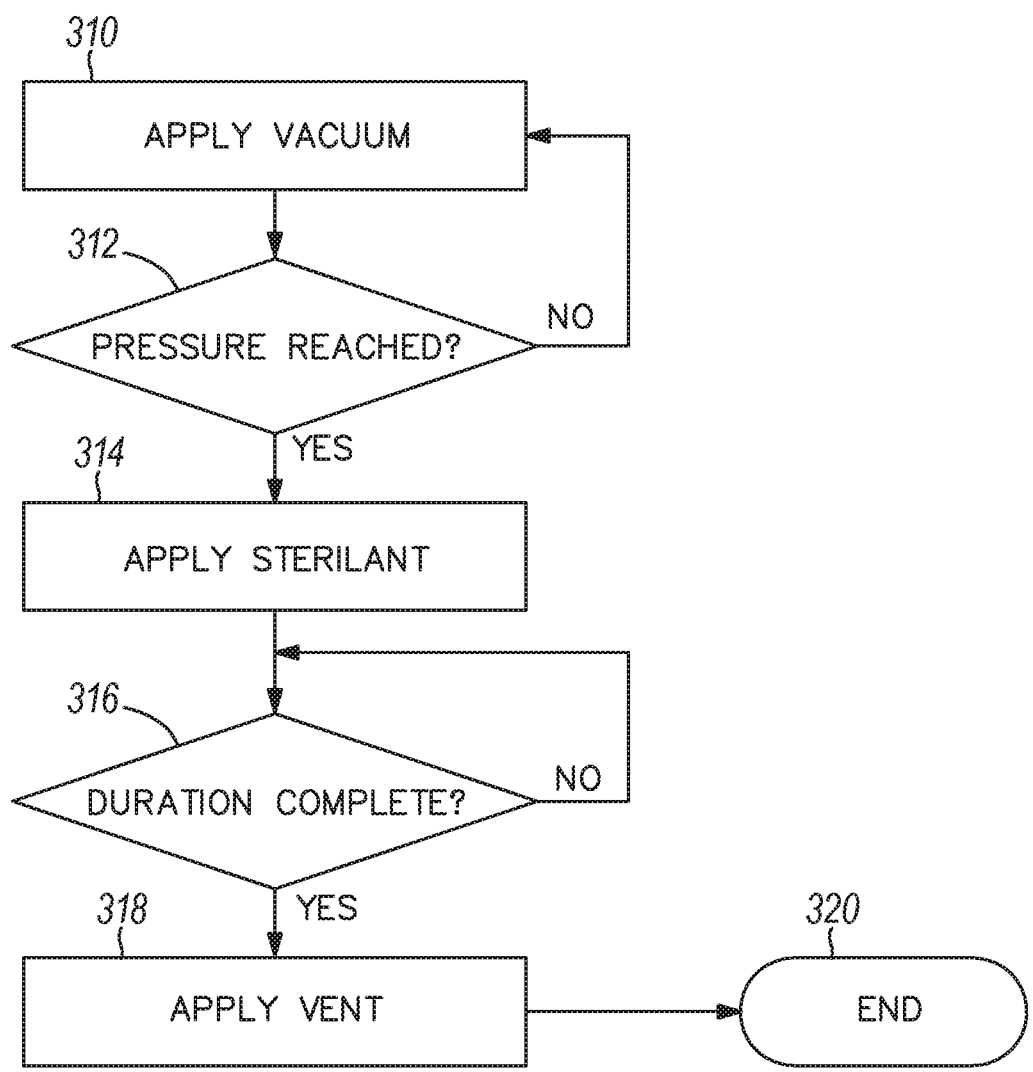
FIG. 3 depicts a flowchart of an exemplary set of steps that may be carried out as part of a first exemplary sterilization cycle within the set of steps of FIG. 2.

In some versions, the sterilization cycle (block 208) includes the exemplary sub-steps shown in FIG. 3. In particular, the cycle may begin with a vacuum being applied (block 310) within sterilization chamber (152). In order to provide such a vacuum, processor (162) may activate vacuum source (180) in accordance with a control algorithm. Processor (162) will then determine (block 312) whether a sufficient pressure level has been reached within sterilization chamber (152). By way of example only, processor (162) may monitor data from one or more pressure sensors within sterilization chamber (152) as part of the determination step (block 312). Alternatively, processor (162) may simply activate vacuum source (180) for a predetermined time period and assume that the appropriate pressure has been reached in sterilization (152) based upon the duration for which vacuum source (180) is activated. Other suitable ways in which processor (162) may determine (block 312) whether a sufficient pressure level has been reached within sterilization chamber (152) will be apparent to those of ordinary skill in the art in view of the teachings herein. Until the appropriate pressure level has been reached within sterilization chamber (152), vacuum source (180) will remain activated.

Once sterilization chamber (152) reaches an appropriate pressure level (e.g., between approximately 0.2 torr and approximately 10 torr), processor (162) then activates sterilization module (156) to apply a sterilant (block 314) in sterilization chamber (152). This stage of the process may be referred to as the "transfer phase." By way of example only, the sterilant may comprise a vapor of oxidizing agent such as hydrogen peroxide, peroxy acids (e.g. peracetic acid, performic acid, etc.), ozone, or a mixture thereof. Furthermore, the sterilant may comprise chlorine dioxide. Various other suitable forms that the sterilant may take are described herein; while other forms will be apparent to those of ordinary skill in the art in view of the teachings herein. It should also be understood that, in some versions, the sterilant may be applied (block 314) in different ways based on the user's selection of cycle (block 200) as described above. Once the sterilant has been applied (block 314) to sterilization chamber (152), processor (162) monitors the time (block 316) to determine whether a sufficient, predetermined duration has passed. By way of example only, this predetermined duration may be anywhere from a few seconds to several minutes. Until the predetermined duration has passed, sterilization chamber (152) remains in a sealed state at the above-noted predetermined pressure level, with the applied sterilant acting upon the medical device(s) contained within sterilization chamber (152).

After the predetermined duration has passed, processor (162) activates (block 318) venting valve (182) to vent sterilization chamber (152) to atmosphere. In some versions, sterilization chamber (152) is allowed to reach atmospheric pressure, while in other versions sterilization chamber (152) only reaches sub-atmospheric pressure. The venting stage of the process may be referred to as the "diffusion phase." In the present example, the sterilization cycle is then complete (block 320) after completion of the diffusion phase. In some other instances, vacuum is again applied to sterilization chamber (152) after completion of the diffusion phase; and then a plasma is applied to sterilization chamber (152). It should be understood that the entire sterilization cycle shown in FIG. 3 (including the above-noted variation where a subsequent vacuum then sterilization is applied) may be repeated one or more times after being completed once. In other words, a medical device may remain within sterilization chamber (152) and experience two or more iterations of the entire cycle shown in FIG. 3 (including the above-noted variation where a subsequent vacuum then sterilization are applied). The number of iterations may vary based on the cycle selection (block 200), which may be influenced by the particular kind of medical device that is being sterilized in sterilization chamber (152).

Figure 4:
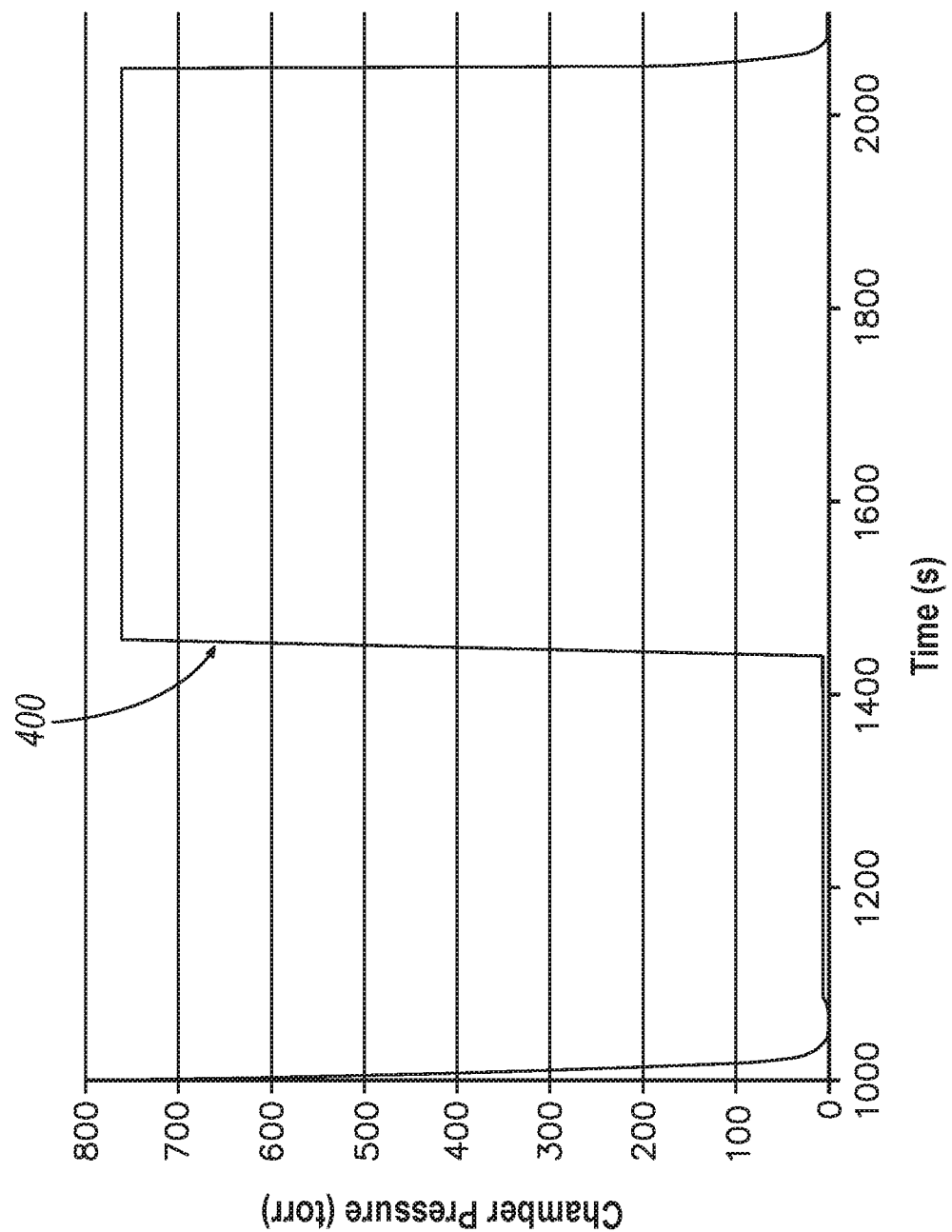
FIG. 4 depicts a graph showing a first exemplary plot of the pressure in a sterilization chamber of the sterilizing cabinet of FIG. 1 over time during performance of the first exemplary sterilization cycle of FIG. 3.

FIG. 4 depicts an exemplary plot (400) showing the pressure within sterilization chamber (152) during performance of the sterilization cycle (block 208) as depicted in FIG. 3 and as described above. As can be seen, the pressure level drops significantly and suddenly when vacuum source (180) is activated to apply vacuum (block 310) to sterilization chamber (152). The pressure level then stays substantially constant while the sterilant is applied (block 314) and during the subsequent, predetermined duration (block 316). The pressure level then increases significantly and suddenly when venting valve (182) is activated (block 318) to vent sterilization chamber (152) to atmosphere. Thus, in general terms, plot (400) shows how the pressure within sterilization chamber (152) simply toggles between a single relatively high level (i.e., atmospheric pressure) and a single relatively low level (i.e., a vacuum state). An exemplary alternative sterilization cycle is described in greater detail below with reference to FIGS. 5-6.

Upon completion of the sterilization cycle (block 208), sterilization cabinet (150) may cycle the results (block 210) of the sterilization cycle (block 208). For instance, if the sterilization cycle (block 208) was canceled or unable to complete due to error or by a user action, sterilizing cabinet (150) may remain sealed and may also display a sterilization cycle cancellation message via touch screen display (160); as well as various details relating to the sterilization cycle, such as date, time, configuration, elapsed time, sterilization cycle operator, the stage at which the sterilization cycle failed, and other information that may be used to identify why the sterilization cycle. If the sterilization cycle (block 208) is completed successfully, sterilization cabinet (150) may display a notification via touch screen display (160) indicating successful completion of the sterilization cycle (block 208). In addition, sterilization cabinet (150) may display information such as sterilization cycle identifier, sterilization cycle type, start time, duration, operator, and other information (666).

In addition to the foregoing, sterilizing cabinet (150) may be configured to perform sterilization processes in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; U.S. Pat. No. 6,447,719, the disclosure of which is incorporated by reference herein; U.S. Pat. No. 6,365,102, the disclosure of which is incorporated by reference herein; U.S. Pat. No. 6,325,972, the disclosure of which is incorporated by reference herein; and/or U.S. Provisional Patent App. No. 62/316,722, the disclosure of which is incorporated by reference herein.

III. Additional Exemplary Alternative Sterilization Cycles

Exemplary methods of sterilizing an article are described in detail below with reference to FIGS. 5-20. While the methods associated with FIGS. 5-20 are described in the context of sterilizing medical devices, and particularly endoscopes, it should be understood that the teachings herein may also be readily applied in the context of sterilizing various other kinds of articles. The teachings are not limited to endoscopes or other medical devices. Other suitable articles that may be sterilized in accordance with the teachings herein will be apparent to those of ordinary skill in the art.

According to an exemplary embodiment, the endoscope may be between 1 meter and 4 meters in length and include a lumen having a diameter of between 0.5 millimeters and 6 millimeters. However, endoscopes of other sizes are also envisioned. Prior to receiving the endoscope in a sterilization chamber, a liquid sterilant may be applied to one or more internal spaces within the endoscope. Instead of or in addition to applying the sterilant to one or more internal spaces within the endoscope, sterilant may be applied to the outside of the endoscope.

Any suitable sterilant may be used in the exemplary methods associated with FIGS. 5-20. By way of example only, the sterilant may comprise a vapor of oxidizing agent such as hydrogen peroxide, peroxy acids (e.g. peracetic acid, performic acid, etc.), ozone, or a mixture thereof. According to an exemplary embodiment, the sterilant may include one or more of hydrogen peroxide, peracetic acid, chlorine dioxide, or nitrogen dioxide. Various other suitable forms that the sterilant may take are described herein; while other forms will be apparent to those of ordinary skill in the art in view of the teachings herein. In successive sterilant introductions, the same sterilant or a different sterilant may be used. As described above, the pressure level stays substantially constant while the sterilant is applied. For example, the pressure within sterilization chamber (152) may rise to approximately 5 torr to approximately 10 torr or so when sterilant is introduced. As used herein, "substantially constant" is intended to include this approximately 5 torr to approximately 10 torr increase in pressure, as there is logically a slight increase in pressure as the sterilant is added as shown in FIGS. 5 and 7-20.

Additional sterilant may be introduced into sterilization chamber (152) while simultaneously venting sterilization chamber (152) to increase the pressure within sterilization chamber (152). Plasma may be applied in any of the exemplary method associated with FIGS. 5-20. For plasma application, a vacuum is first applied to sterilization chamber (152) to reduce the pressure within sterilization chamber (152). For example, vacuum may be applied to sterilization chamber (152) to reduce the pressure to approximately 0 torr to approximately 5 torr. Once the vacuum is applied, plasma may be then applied to sterilization chamber (152). In an instance, plasma may be applied below approximately 3 torr or so, and in another instance plasma may be applied between a pressure of approximately 0.15 torr and approximately 2 torr. Sterilization chamber (152) may be vented to a pressure of between 10 torr and atmospheric pressure (ATM) after applying the additional plasma to sterilization chamber (152). Multiple vents, in a stepwise fashion or other pattern, may be utilized in any of the exemplary methods of FIGS. 5-20. The upper dashed horizontal line on FIGS. 7-10 and 12-20 represents atmospheric pressure (ATM), and the lower dashed horizontal line on FIGS. 7-10 and 12-20 represents a lower pressure, shown as 100 torr. Alternatively, other lower pressures (e.g. 50 torr) are also envisioned. A break is shown between the upper and lower dashed horizontal lines of FIGS. 7-10 and 12-20.

One or more of the steps may be controlled automatically in any of the exemplary methods associated with of FIGS. 5-20. For example, the step(s) may be controlled automatically using a controller that includes a processor and memory. A notification may be displayed indicating successful completion of the sterilization using a touch screen display. The notification may include at least one of sterilization cycle type, start time, or duration. A sterilization cancellation message may be displayed using a touch screen display. For example, at least one of elapsed time, sterilization operator, or the step at which the sterilization failed may be displayed using the touch screen display. The level of moisture within sterilization chamber (152) may be monitored while reducing the level of moisture within sterilization chamber (152) until a predetermined level of moisture has been reached.

A. First Exemplary Alternative Sterilization Cycle

As noted above, some versions of sterilizing cabinet (150) may have difficulty effectively sterilizing some articles including medical devices such as flexible endoscopes with relatively long, narrow lumens. For instance, some conventional sterilizing cabinets may be capable of sterilizing lumens that are shorter than or equal to approximately 875 millimeters, with a lumen diameter of approximately 1 millimeter or larger. It may therefore be desirable to provide a modified sterilization cycle (block 208) that further promotes effective sterilization of a medical device having one or more relatively long, narrow lumens. A merely illustrative example of such a modified sterilization cycle is described in greater detail below. By way of example only, a medical device having one or more relatively long, narrow lumens may comprise a gastrointestinal endoscope that is between approximately 1 meter long and approximately 3 meters long, with a lumen having a diameter between approximately 0.5 millimeters and approximately 2.0 millimeters. It should nevertheless be understood that the process described below may also be performed on endoscopes having a length of at least approximately 500 millimeters or at least approximately 800 millimeters, with a lumen having a diameter less than approximately 6.0 millimeters.

Figure 5:
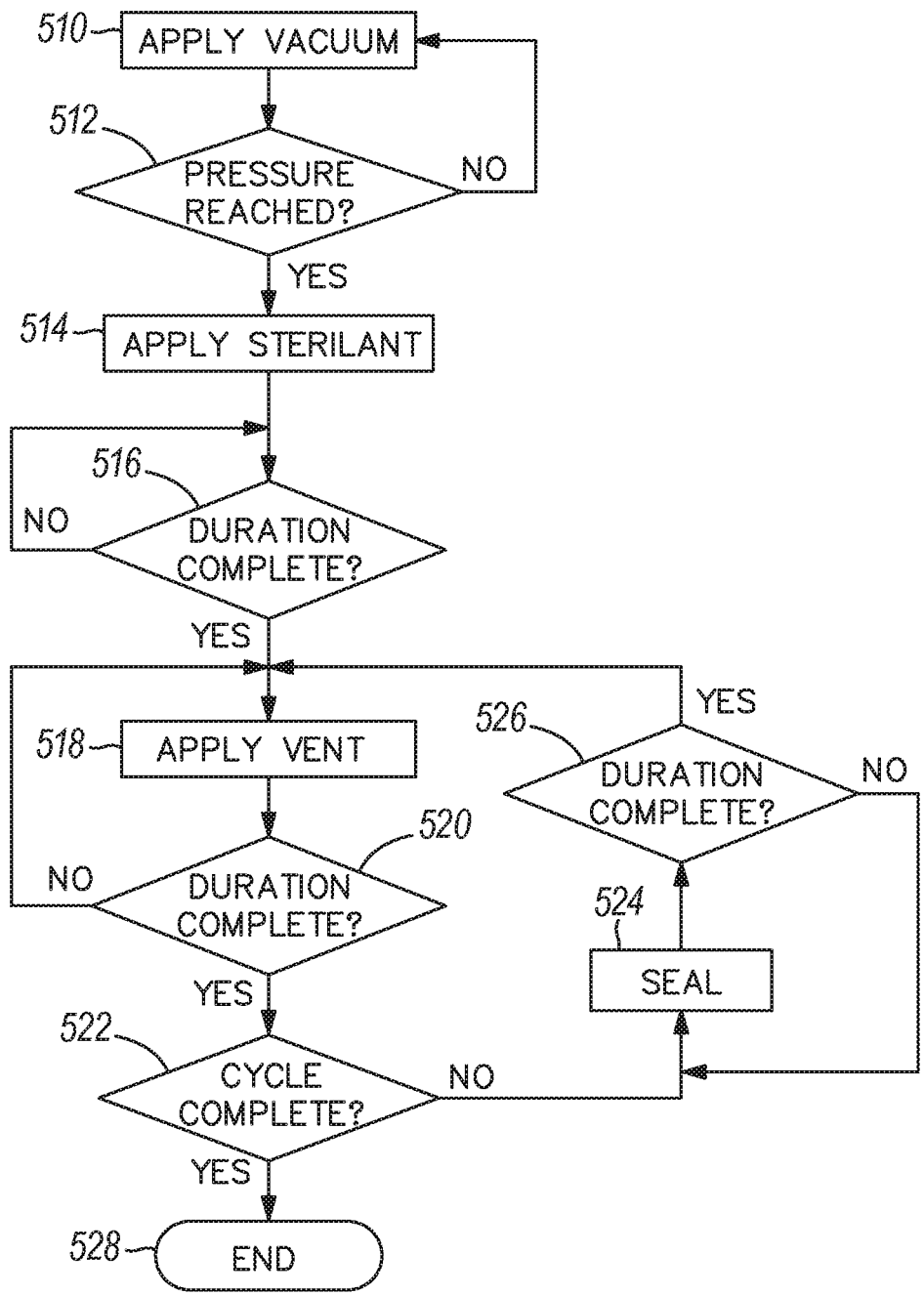
FIG. 5 depicts a flowchart of an exemplary alternative set of steps that may be carried out as part of a first exemplary alternative sterilization cycle within the set of steps of FIG. 2.

FIG. 5 shows an exemplary alternative set of sub-steps that may be performed to provide the sterilization cycle (block 208) of sterilizing cabinet (150). In particular, the cycle shown in FIG. 5 may begin with a vacuum being applied (block 510) within sterilization chamber (152). In order to provide such a vacuum, processor (162) may activate vacuum source (180) in accordance with a control algorithm. Processor (162) will then determine (block 512) whether a sufficient pressure level has been reached within sterilization chamber (152). By way of example only, processor (162) may monitor data from one or more pressure sensors within sterilization chamber (152) as part of the determination step (block 512). Alternatively, processor (162) may simply activate vacuum source (180) for a predetermined time period and assume that the appropriate pressure has been reached in sterilization (152) based upon the duration for which vacuum source (180) is activated. Other suitable ways in which processor (162) may determine (block 512) whether a sufficient pressure level has been reached within sterilization chamber (152) will be apparent to those of ordinary skill in the art in view of the teachings herein. Until the appropriate pressure level has been reached within sterilization chamber (152), vacuum source (180) will remain activated.

Once sterilization chamber (152) reaches an appropriate pressure level (e.g., between approximately 0.2 torr and approximately 10 torr), processor (162) then activates sterilization module (156) to apply a sterilant (block 514) in sterilization chamber (152). It should also be understood that, in some versions, the sterilant may be applied (block 514) in different ways based on the user's selection of cycle (block 200) as described above. Once the sterilant has been applied (block 514) to sterilization chamber (152), processor (162) monitors the time (block 516) to determine whether a sufficient, predetermined duration has passed. By way of example only, this predetermined duration may be anywhere from a few seconds to several minutes. Until the predetermined duration has passed, sterilization chamber (152) remains in a sealed state at the above-noted predetermined pressure level, with the applied sterilant acting upon the medical device(s) contained within sterilization chamber (152). This stage of the process may be referred to as the "transfer phase."

After the predetermined duration has passed, processor (162) activates (block 518) venting valve (182) to vent sterilization chamber (152) to atmosphere. With sterilization chamber (152) being vented (block 518) to atmosphere, processor (162) monitors the time (block 520) to determine whether a sufficient, predetermined venting (block 518) duration has passed. Until the predetermined venting (block 518) duration has passed, sterilization chamber (152) remains in a vented state. After the predetermined venting (block 518) duration has passed, processor (162) determines (block 522) whether the sterilization cycle is complete. Examples of how this determination (block 522) may be made will be described in greater detail below. It should be understood that, in the present example, the predetermined venting (block 518) duration may be very brief. By way of example only, the predetermined venting (block 518) duration may be approximately one second, two seconds, three seconds, four seconds, five seconds, or any other suitable duration.

If processor (162) determines (block 522) that the sterilization cycle is complete, then the sterilization cycle is in fact complete (block 528). However, if processor (162) determines (block 522) that the sterilization cycle is not yet complete, then processor (162) closes venting valve (182) to seal (block 524) sterilization chamber (152) at a pressure level that is still less than atmospheric pressure. As noted above, the venting (block 518) duration is very short in this example, such that the act of sealing (block 524) may occur very quickly after venting (block 518) is initiated, assuming that the determinations (block 520, 522) confirm that sealing (block 524) is in order.

Sterilization chamber (152) will remain sealed (block 524) for a certain period of time. In particular, with sterilization chamber (152) being sealed (block 524), processor (162) monitors the time (block 526) to determine whether a sufficient, predetermined sealing (block 524) duration has passed. Until the predetermined sealing (block 524) duration has passed, sterilization chamber (152) remains in a sealed state. After the predetermined sealing (block 524) duration has passed, processor (162) activates (block 518) venting valve (182) again to vent sterilization chamber (152) to atmosphere. By way of example only, the predetermined sealing duration may be between approximately 5 seconds and 5 minutes, or more particularly between approximately 10 seconds and approximately 2 minutes, or more particularly between approximately 20 seconds and approximately 2 minutes.

At this point the process continues through the steps (blocks 518, 520, 522, 524, 526) described above, such that the process provides a series of venting (block 518) and sealing (block 524) of sterilization chamber (152), allowing the pressure within sterilization chamber (152) to increase in a stepwise fashion until sterilization chamber (152) reaches atmospheric pressure or some predetermined sub-atmospheric pressure. Again, each step of venting (block 518) is very brief in this example, such that the pressure of sterilization chamber (152) is held at levels below atmospheric pressure during the acts of sealing (block 524) (e.g., for a duration between approximately a few seconds or a few minutes). By way of example only, until the final step of venting (block 518) is reached, each step of venting (block 518) may result in a respective increase in the pressure within sterilization chamber (152) by approximately 10 torr to approximately 100 torr, or more particularly by approximately 10 torr to approximately 30 torr. Other suitable stepwise pressure increase values will be apparent to those of ordinary skill in the art in view of the teachings herein. Once sterilization cabinet (150) reaches the end of the process, venting valve (182) remains open to allow sterilization chamber (152) to remain at atmospheric pressure. The final venting step (block 518) of the process may be referred to as the "diffusion phase."

In some versions, the venting duration (block 520) and/or the sealing duration (block 526) may vary. For instance, the venting duration (block 520) and/or the sealing duration (block 526) may vary based on the cycle selection (block 200), which may be influenced by the particular kind of medical device that is being sterilized in sterilization chamber (152). In addition, or in the alternative, the venting duration (block 520) and/or the sealing duration (block 526) may vary based on where the sterilization cycle is at in the process (i.e., which venting (block 518) iteration and/or which sealing (block 524) iteration). Various suitable ways in which the venting duration (block 520) and/or the sealing duration (block 526) may vary, and various bases upon which such durations may vary, will be apparent to those of ordinary skill in the art in view of the teachings herein.

Figure 6:
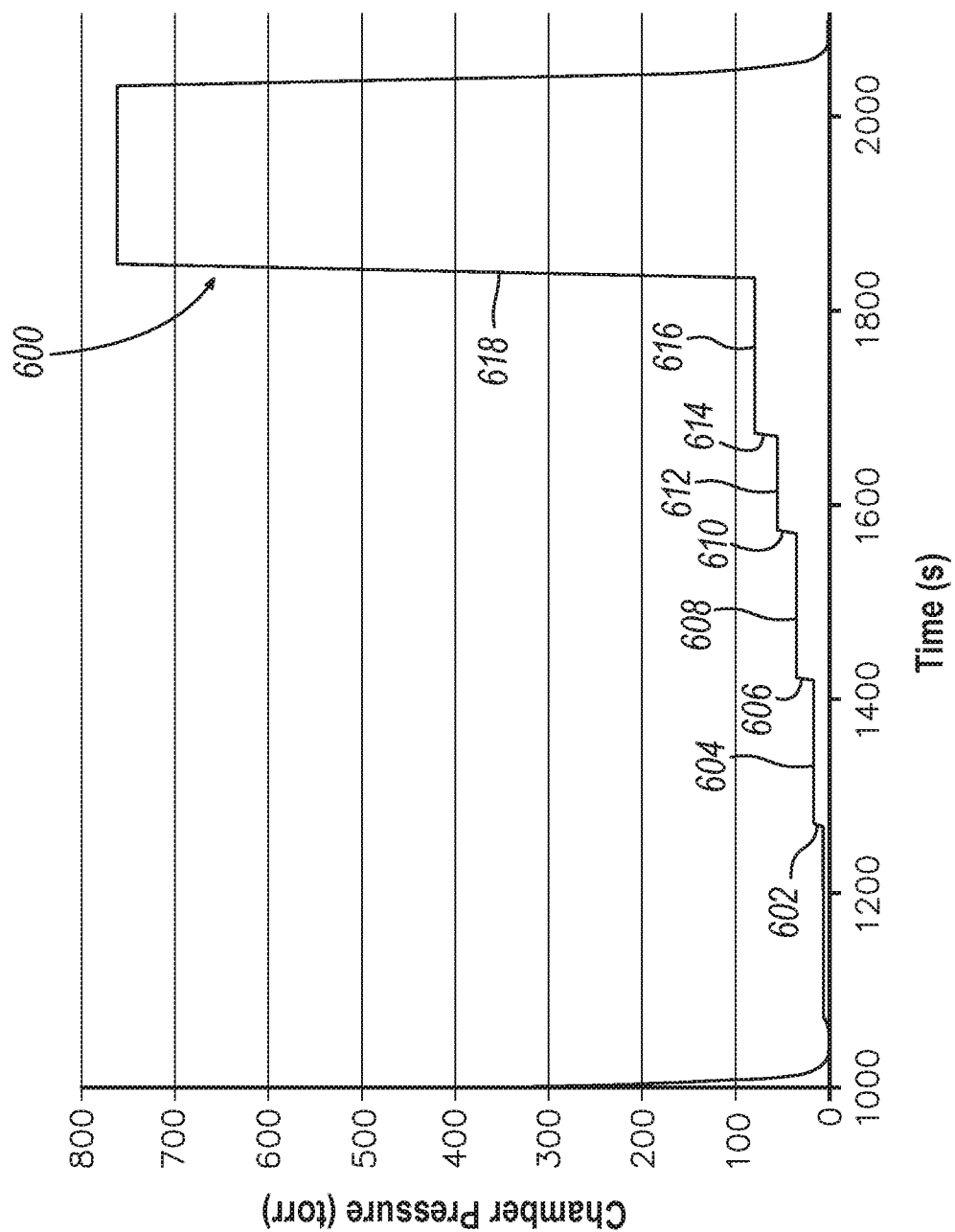
FIG. 6 depicts a graph showing a second exemplary plot of the pressure in a sterilization chamber of the sterilizing cabinet of FIG. 1 over time during performance of the first exemplary alternative sterilization cycle of FIG. 5.

FIG. 6 shows an exemplary plot (600) showing the pressure within sterilization chamber (152) during performance of the sterilization cycle (block 208) as depicted in FIG. 5 and as described above. As can be seen, the pressure level drops significantly and suddenly when vacuum source (180) is activated to apply vacuum (block 510) to sterilization chamber (152). The pressure level then stays substantially constant while the sterilant is applied (block 514) and during the subsequent, predetermined duration (block 516). The pressure level then increases slightly when venting valve (182) is activated (block 518) to vent sterilization chamber (152) to atmosphere; yet stays at a level below atmosphere when sterilization chamber (152) is sealed (block 524). The pressure level then again increases slightly when venting valve (182) is again activated (block 518) to vent sterilization chamber (152) to atmosphere; yet still stays at a level below atmosphere when sterilization chamber (152) is again sealed (block 524).

In the example shown in FIG. 6, the cycle provides four iterations of brief venting (block 518), followed by four iterations of sealing (block 524), before finally venting (block 518) fully to atmosphere. Thus, in general terms, plot (600) shows how the pressure within sterilization chamber (152) is increased in a stepwise fashion from a substantial vacuum state to atmospheric pressure. While FIG. 6 shows four iterations of brief venting (602, 606, 610, 614) and brief sealing (604, 608, 612, 616) and subsequently venting to atmosphere (618), other processes may employ any other suitable number of iterations of brief venting and brief sealing. Optionally, atmospheric pressure may be maintained for a period of time before proceeding with another cycle (with application of the vacuum being shown in FIG. 5). By way of example only, variations may provide anywhere between two iterations of brief venting and brief sealing and 100 iterations of brief venting and brief sealing, or more particularly between two iterations of brief venting and brief sealing and ten iterations of brief venting and brief sealing, or more particularly between three iterations of brief venting and brief sealing and seven iterations of brief venting and brief sealing.

In some instances, the process shown in FIGS. 5-6 may provide more effective sterilization of some medical devices as compared to the sterilization of the same medical devices using the process shown in FIGS. 3-4. In particular, and without being limited by theory, the step-wise venting of sterilization chamber (152) may provide agitation of the contents of sterilization chamber (152), which may assist in driving the sterilant into the lumen(s) and/or other internal spaces within the medical device. Moreover, and again without being limited by theory, the step-wise venting of sterilization chamber (152) associated with the process shown in FIGS. 5-6 may provide convective mass transfer of sterilant vapor molecules inside the lumen(s) and/or other internal spaces within the medical device; as compared to the simple diffusive mass transfer of vapor associated with the process shown in FIGS. 3-4. Thus, when sterilization cabinet (150) performs the process shown in FIGS. 5-6, sterilization cabinet (150) may sterilize a relatively long gastrointestinal endoscope (e.g., up to approximately 3 meters in length and with a lumen having a diameter up to approximately 1 millimeters); as compared to sterilization cabinet (150) performing the process shown in FIGS. 3-4, which would not be able to sterilize the long, narrow lumens of the same kind of gastrointestinal endoscope.

It should also be understood that the entire cycle shown in FIGS. 5-6 may be repeated one or more times after being completed once. In other words, a medical device may remain within sterilization chamber (152) and experience two or more iterations of the entire cycle shown in FIGS. 5-6. The number of iterations may vary based on the cycle selection (block 200), which may be influenced by the particular kind of medical device that is being sterilized in sterilization chamber (152). This also applies to any exemplary method shown in plots (700, 800, 900, 1000, 1100, 1200, 1300, 1400, 1500, 1600, 1700, 1800, 1900, 2000) of FIGS. 7-20.

By way of example only, an endoscope with a 3 m long lumen may be placed in sterilization chamber (152). Vacuum may be applied (block 510) to achieve a pressure level of approximately 4.5 torr in sterilization chamber (152). Sterilant (e.g., approximately 1 mL of a hydrogen peroxide vapor at a concentration of 59%) may then be applied (block 514) to provide a transfer phase lasting approximately 30 seconds. Sterilization chamber (152) may then be briefly vented (block 518) to achieve a pressure level of approximately 13.7 torr, and then sterilization chamber (152) may be sealed (block 524). Sterilization chamber (152) may be held at the approximately 13.7 torr for approximately 150 seconds. Sterilization chamber (152) may then be briefly vented (block 518) again to achieve a pressure level of approximately 30.1 torr, and then sterilization chamber (152) may be sealed (block 524) again. Sterilization chamber (152) may be held at the approximately 30.1 torr for approximately 200 seconds. Sterilization chamber (152) may then be briefly vented (block 518) again to achieve a pressure level of approximately 47.1 torr, and then sterilization chamber (152) may be sealed (block 524) again. Sterilization chamber (152) may be held at the approximately 47.1 torr for approximately 190 seconds. Sterilization chamber (152) may then be briefly vented (block 518) again to achieve a pressure level of approximately 760 torr (i.e., atmospheric pressure), thereby providing a diffusion phase. Of course, the foregoing is just one merely illustrative example.

As described above, in some variations, before the final step of venting (block 518) is reached, additional sterilant is introduced into sterilization chamber (152) during one or more of the acts of stepwise venting (block 518). This also applies to any exemplary method shown in plots (700, 800, 900, 1000, 1100, 1200, 1300, 1400, 1500, 1600, 1700, 1800, 1900, 2000) of FIGS. 7-20.

As described above, in some variations, a pre-plasma may be applied in the sterilization cycle (block 208) to heat up the medical device contained in sterilization chamber (152). By way of example only, plasma may be applied between applying a vacuum (block 510) and applying sterilant (block 514). In addition, or in the alternative, a post-plasma may be applied at the end of the sterilization cycle (block 208) to degrade any residual sterilant that may be adsorbed to the surface of the medical device contained in sterilization chamber (152). It should be understood that, before applying the post-plasma, a vacuum would first need to be applied to sterilization chamber (152). This also applies to any exemplary method shown in plots (700, 800, 900, 1000, 1100, 1200, 1300, 1400, 1500, 1600, 1700, 1800, 1900, 2000) of FIGS. 7-20.

As noted above, the sterilant is applied (block 514) in the form of a vapor within sterilization chamber (152). By way of example only, sterilization module (156) may comprise a combination of a vaporizer and a condenser. The vaporizer may include a chamber that receives a particular concentration of sterilant solution (e.g., a liquid hydrogen peroxide solution with a concentration of approximately 59% nominal, or between approximately 58% and approximately 59.6%); where the sterilant solution changes phase from liquid to vapor. The condenser may provide condensation of the sterilant solution vapor, and the concentration of the sterilant solution may be thereby increased (e.g., from approximately 59% nominal to somewhere between approximately 83% nominal and approximately 95% nominal), by removal of water vapor. Alternatively, any other suitable methods and components may be used to apply sterilant in the form of a vapor within sterilization chamber (152). In any case, to supplement the application of the sterilant in the form of a vapor, the sterilant may also be applied (in liquid form) to the inside of lumen(s) and/or other internal spaces within the medical device and/or the outside of the medical device, before the medical device is placed in sterilization chamber (152). In such versions, the sterilant may evaporate while vacuum is applied (block 510) and even after vacuum is applied (block 510); and provide more concentration of sterilant to the areas of the medical device with less penetration range, thereby further promoting effective sterilization.

By way of example only, the process depicted in FIG. 5 may be carried out at temperatures where the walls of sterilization chamber (152) are between approximately 30° C. and approximately 56° C., or more particularly between approximately 47° C. and approximately 56° C., or even more particularly approximately 50° C.; and where the temperature of the medical device in sterilization chamber (152) is between approximately 5-10° C. and approximately 40-55° C.

C. Second Exemplary Alternative Sterilization Cycle

Figure 7:
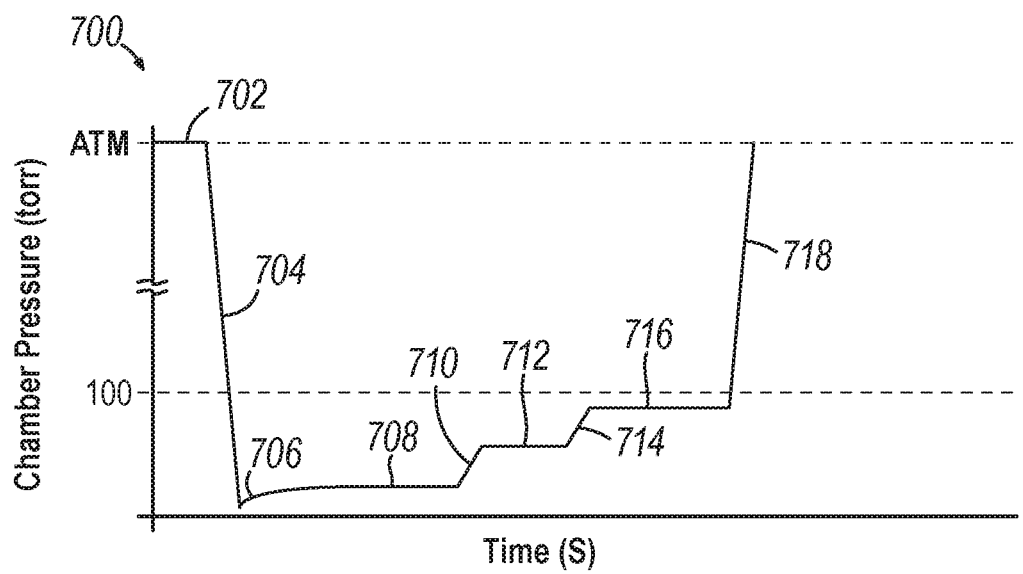
FIG. 7 depicts a graph showing a third exemplary plot of the pressure in a sterilization chamber of the sterilizing cabinet of FIG. 1 over time during performance of a second exemplary alternative sterilization cycle.

FIG. 7 depicts a graph showing a third exemplary plot (700) of the pressure in sterilization chamber (152) of sterilizing cabinet (150) of FIG. 1 over time during performance of a second exemplary alternative sterilization cycle. As described above, the sterilization cycle method associated with FIG. 7 may be performed on an endoscope or any other kind of article.

At step (702), the method shown in plot (700) includes receiving the endoscope in a sterilization chamber. At step (704), the method shown in plot (700) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat the chamber or the gas that introduced during venting. For example, vacuum may be applied to sterilization chamber (152) to reduce the pressure to approximately 0 torr to approximately 5 torr. At step (706), the method shown in plot (700) includes introducing a sterilant into sterilization chamber (152). Any suitable sterilant may be used.

At step (708), the method shown in plot (700) includes maintaining the first pressure in sterilization chamber (152) for a first period of time. At step (710), the method shown in plot (700) includes venting sterilization chamber (152) to increase the pressure within sterilization chamber (152) to a second pressure. The second pressure is greater than the first pressure, but the second pressure is still less than 100 torr. Once again, at or below 100 torr, condensation is prevented without the need to either heat the chamber or the gas that introduced during venting. For example, in some instances the second pressure may be approximately 5 torr to 30 torr greater than the first pressure, and in some instances the second pressure may be between approximately 10 torr to approximately 15 torr greater than the first pressure. The second pressure is not dependent on a temperature of sterilization chamber (152). At step (712), the method shown in plot (700) includes maintaining the second pressure in sterilization chamber (152) for a second period of time. The second period of time may be shorter or longer than the first period of time Additional steps may be added before method shown in plot (700), in the middle of method shown in plot (700), and after completing method shown in plot (700). For example, variations may include one or more steps before or after vacuum step (704) or one or more steps before or after venting steps (710, 714, 718).

D. Third Exemplary Alternative Sterilization Cycle

Figure 8:
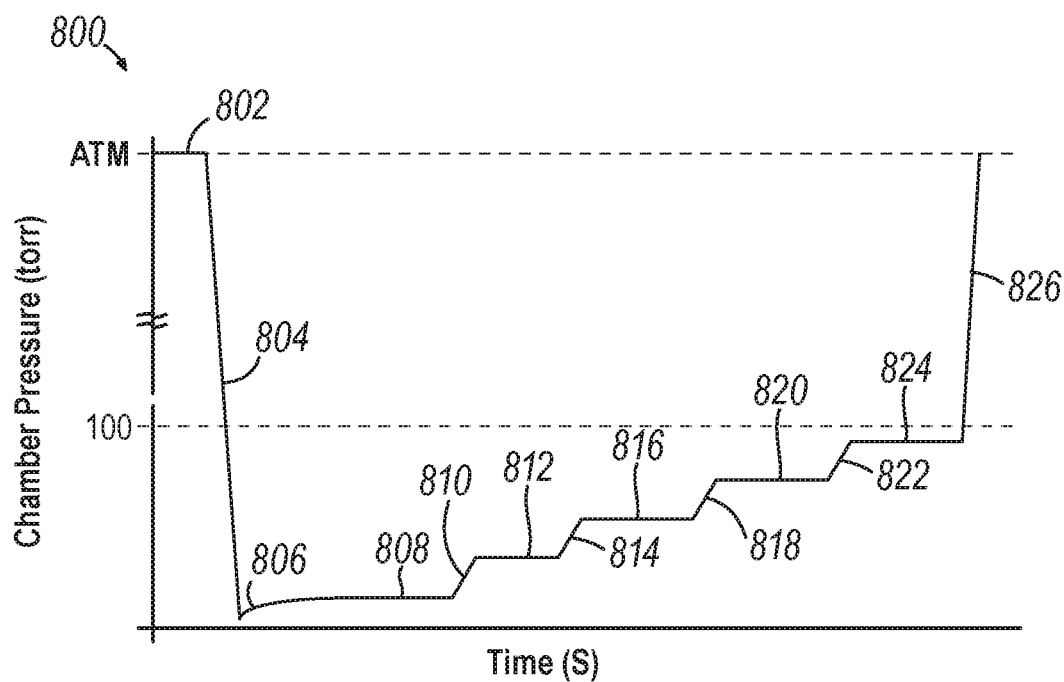
FIG. 8 depicts a graph showing a fourth exemplary plot of the pressure in a sterilization chamber of the sterilizing cabinet of FIG. 1 over time during performance of a third exemplary alternative sterilization cycle.

FIG. 8 depicts a graph showing a fourth exemplary plot (800) of the pressure in sterilization chamber (152) of sterilizing cabinet (150) of FIG. 1 over time during performance of a third exemplary alternative sterilization cycle. As described above, the sterilization cycle method associated with FIG. 8 may be performed on an endoscope or any other kind of article.

For example, the article may include an endoscope. At step (802), the method shown in plot (800) includes receiving the endoscope in a sterilization chamber. At step (804), the method shown in plot (800) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat the chamber or the gas that introduced during venting. Vacuum may be applied until the pressure of sterilization chamber (152) is far below 100 torr. For example, vacuum may be applied to sterilization chamber (152) to reduce the pressure to approximately 0 torr to approximately 5 torr. At step (806), the method shown in plot (800) includes introducing a sterilant into sterilization chamber (152). At step (808), the method shown in plot (800) includes maintaining the first pressure in sterilization chamber (152) for a first period of time.

At step (810), the method shown in plot (800) includes venting sterilization chamber (152) to increase the pressure within sterilization chamber (152) to a second pressure. The second pressure is greater than the first pressure, but the second pressure is still less than 100 torr. Once again, at or below 100 torr, condensation is prevented without the need to either heat sterilization chamber (152) or the gas that introduced during the venting step(s). For example, in some instances, the second pressure may be approximately 5 torr to approximately 30 torr greater than the first pressure, and in some instances the second pressure may be between approximately 10 torr to approximately 15 torr greater than the first pressure. At step (812), the method shown in plot (800) includes maintaining the second pressure in sterilization chamber (152) for a second period of time. The second period of time may be shorter or longer than the first period of time.

At step (814), the method shown in plot (800) includes venting sterilization chamber (152) to increase the pressure within sterilization chamber (152) to a third pressure. The third pressure is less than 100 torr. For example, in some instances, the third pressure may be approximately 5 torr to approximately 30 torr greater than the second pressure, and in some instances, the third pressure may be between approximately 10 torr to approximately 15 torr greater than the second pressure. At step (816), the method shown in plot (800) includes maintaining the third pressure in sterilization chamber (152) for a third period of time. The third period of time may be shorter or longer than any one of the first or second periods of time.

At step (818), the method shown in plot (800) includes venting sterilization chamber (152) to increase the pressure within sterilization chamber (152) to a fourth pressure. The fourth pressure is less than 100 torr. Once again, at or below 100 torr, condensation is prevented without the need to either heat sterilization chamber (152) or the gas that introduced during the venting step(s). For example, in some instances the fourth pressure may be approximately 5 torr to approximately 30 torr greater than the third pressure, and in some instances the fourth pressure may be between approximately 10 torr to approximately 15 torr greater than the third pressure. The pressure difference in the first and second vents in steps (814, 818) may be the same or different. At step (820), the method shown in plot (800) includes maintaining the fourth pressure in sterilization chamber (152) for a fourth period of time. The fourth period of time may be shorter or longer than any one of the first, second, or third periods of time.

At step (822), the method shown in plot (800) includes venting sterilization chamber (152) to increase the pressure within sterilization chamber (152) to a fifth pressure. The fifth pressure is less than 100 torr. For example, in some instances the fifth pressure may be approximately 5 torr to approximately 30 torr greater than the fourth pressure, and in some instances the fifth pressure may be between approximately 10 torr to approximately 15 torr greater than the fourth pressure. At step (824), the method shown in plot (800) includes maintaining the fifth pressure in sterilization chamber (152) for a fifth period of time. In some versions, one or more of steps (808, 812, 816, 820, 824) may have a duration ranging from approximately 30 seconds to approximately 300 seconds.

At step (826), the method shown in plot (800) includes venting sterilization chamber (152) to increase the pressure within sterilization chamber (152) to a sixth pressure, shown as atmospheric pressure (ATM). While not shown, in some instances the sixth pressure may be approximately 5 torr to approximately 30 torr greater than the fifth pressure, and in some instances the sixth pressure may be between approximately 10 torr to approximately 15 torr greater than the fifth pressure.

While method steps (802, 804, 806, 808, 810, 812, 814, 816, 818, 820, 822, 824, 826) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (800), in the middle of the method shown in plot (800), and after completing the method shown in plot (800). For example, variations may include one or more steps before or after vacuum step (804) or one or more steps before or after venting steps (810, 814, 818, 822, 826).

E. Fourth Exemplary Alternative Sterilization Cycle

Figure 9:
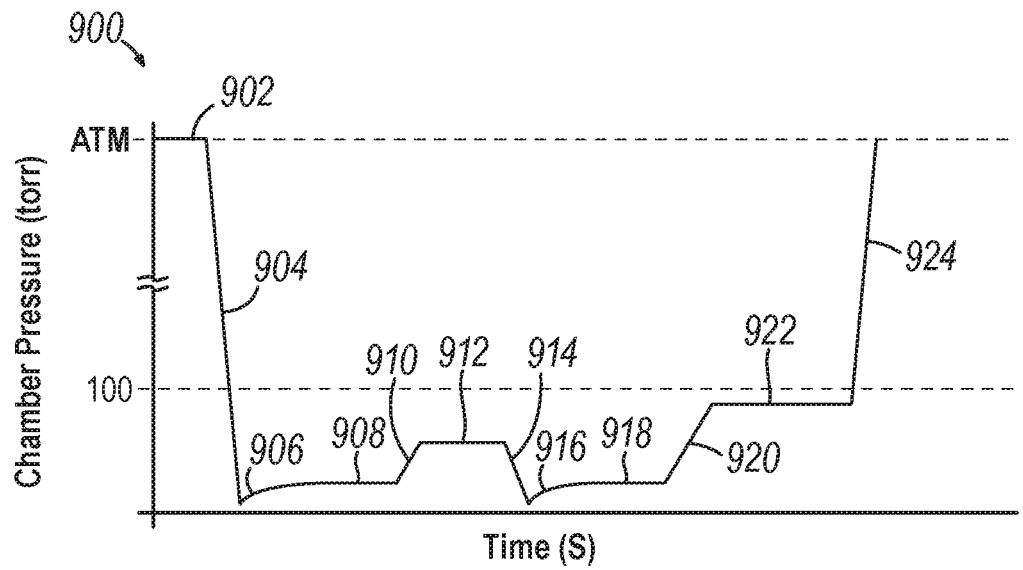
FIG. 9 depicts a graph showing a fifth exemplary plot of the pressure in a sterilization chamber of the sterilizing cabinet of FIG. 1 over time during performance of a fourth exemplary alternative sterilization cycle.

FIG. 9 depicts a graph showing a fifth exemplary plot (900) of the pressure in sterilization chamber (152) of sterilizing cabinet (150) of FIG. 1 over time during performance of a fourth exemplary alternative sterilization cycle. As described above, the sterilization cycle method associated with FIG. 9 may be performed on an endoscope or any other kind of article.

At step (902), the method shown in plot (900) includes receiving the endoscope in a sterilization chamber. At step (904), the method shown in plot (900) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to the chamber to reduce the pressure to approximately 0 torr to approximately 5 torr. At step (906), the method shown in plot (900) includes introducing a sterilant into sterilization chamber (152). At step (908), the method shown in plot (900) includes maintaining the first pressure in sterilization chamber (152) for a first period of time.

At step (910), the method shown in plot (900) includes venting sterilization chamber (152) to increase the pressure within sterilization chamber (152) to a second pressure. The second pressure is greater than the first pressure but is still less than 100 torr. For example, in some instances the second pressure may be approximately 5 torr to approximately 30 torr greater than the first pressure, and in some instances the second pressure may be between approximately 10 torr to approximately 15 torr greater than the first pressure. At step (912), the method shown in plot (900) includes maintaining the second pressure in sterilization chamber (152) for a second period of time. The second period of time may be shorter or longer than the first period of time.

At step (914), the method shown in plot (900) includes applying a vacuum to sterilization chamber (152) to reduce the pressure within sterilization chamber (152) to a third pressure. The third pressure is less than 100 torr. For example, vacuum may be applied to sterilization chamber (152) to reduce the pressure to approximately 0 torr to approximately 5 torr. At step (916), the method shown in plot (900) includes introducing a sterilant into sterilization chamber (152). At step (918), the method shown in plot (900) includes maintaining the third pressure in sterilization chamber (152) for a third period of time. The third period of time may be shorter or longer than any one of the first or second periods of time.

At step (920), the method shown in plot (900) includes venting sterilization chamber (152) to increase the pressure within sterilization chamber (152) to a fourth pressure. For example, in some instances the fourth pressure may be approximately 5 torr to approximately 30 torr greater than the third pressure, and in some instances the fourth pressure may be between approximately 10 torr to approximately 15 torr greater than the third pressure. The fourth pressure may be greater than or less than the second pressure. At step (922), the method shown in plot (900) includes maintaining the fourth pressure in sterilization chamber (152) for a fourth period of time. The fourth period of time may be shorter or longer than any one of the first, second, or third periods of time. In some versions, one or more of steps (908, 912, 918, 922) may have a duration ranging from approximately 30 seconds to approximately 300 seconds.

At step (924), the method shown in plot (900) includes venting sterilization chamber (152) to increase the pressure within sterilization chamber (152) to a fifth pressure, shown as atmospheric pressure (ATM). While not shown, in some instances the fifth pressure may be approximately 5 torr to approximately 30 torr greater than the fourth pressure, and in some instances the fifth pressure may be between approximately 10 torr to approximately 15 torr greater than the fourth pressure.

While method steps (902, 904, 906, 908, 910, 912, 914, 916, 918, 920, 922, 924) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (900), in the middle of the method shown in plot (900), and after completing the method shown in plot (900). For example, variations may include one or more steps before or after vacuum step (904) or one or more steps before or after venting steps (910, 920, 924).

F. Fifth Exemplary Alternative Sterilization Cycle

Figure 10:
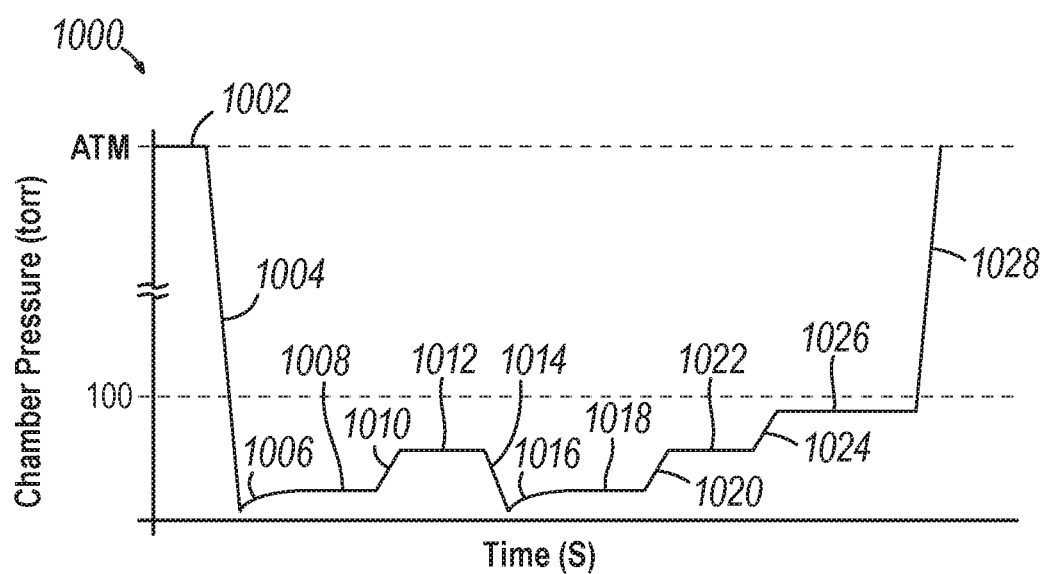
FIG. 10 depicts a graph showing a sixth exemplary plot of the pressure in a sterilization chamber of the sterilizing cabinet of FIG. 1 over time during performance of a fifth exemplary alternative sterilization cycle.

FIG. 10 depicts a graph showing a sixth exemplary plot (1000) of the pressure in sterilization chamber (152) of sterilizing cabinet (150) of FIG. 1 over time during performance of a fifth exemplary alternative sterilization cycle. As described above, the sterilization cycle method associated with FIG. 10 may be performed on an endoscope or any other kind of article.

At step (1002), the method shown in plot (1000) includes receiving the endoscope in a sterilization chamber. At step (1004), the method shown in plot (1000) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1006), the method shown in plot (1000) includes introducing a sterilant into sterilization chamber (152). At step (1008), the method shown in plot (1000) includes maintaining the first pressure in sterilization chamber (152) for a first period of time.

At step (1010), the method shown in plot (1000) includes venting sterilization chamber (152) to increase the pressure within sterilization chamber (152) to a second pressure. The second pressure is greater than the first pressure but is still less than 100 torr. Once again, at or below 100 torr, condensation is prevented without the need to either heat sterilization chamber (152) or the gas that introduced during the venting step(s). For example, in some instances the second pressure may be approximately 10 torr to 100 torr greater than the first pressure, and in some instances the second pressure may be between approximately 10 torr to approximately 30 torr greater than the first pressure. At step (1012), the method shown in plot (1000) includes maintaining the second pressure in sterilization chamber (152) for a second period of time. The second period of time may be shorter or longer than the first period of time.

At step (1014), the method shown in plot (1000) includes applying a vacuum to sterilization chamber (152) to reduce the pressure within sterilization chamber (152) to a third pressure. The third pressure is less than 100 torr. For example, a vacuum may be applied to sterilization chamber (152) to reduce the pressure to approximately 0 torr to approximately 5 torr. At step (1016), the method shown in plot (1000) includes introducing additional sterilant into sterilization chamber (152). The same or different sterilant may be used from step (1006). At step (1018), the method shown in plot (1000) includes maintaining the third pressure in sterilization chamber (152) for a third period of time. The third period of time may be shorter or longer than the first or second periods of time.

At step (1020), the method shown in plot (1000) includes venting sterilization chamber (152) to increase the pressure within sterilization chamber (152) to a fourth pressure. The fourth pressure is greater than the third pressure but is still less than 100 torr. For example, in some instances the fourth pressure may be approximately 5 torr to approximately 30 torr greater than the third pressure, and in some instances the fourth pressure may be between approximately 10 torr to approximately 15 torr greater than the third pressure. The fourth pressure may be greater than or less than the second pressure shown in step (1012). At step (1022), the method shown in plot (1000) includes maintaining the fourth pressure in sterilization chamber (152) for a fourth period of time. The fourth period of time may be shorter or longer than the any one of the first, second, or third periods of time.

At step (1024), the method shown in plot (1000) includes venting sterilization chamber (152) to increase the pressure within sterilization chamber (152) to a fifth pressure. For example, in some instances the fifth pressure may be approximately 5 torr to approximately 30 torr greater than the fourth pressure, and in some instances the fifth pressure may be between approximately 10 torr to approximately 15 torr greater than the fourth pressure. At step (1026), the method shown in plot (1000) includes maintaining the fifth pressure in sterilization chamber (152) for a fifth period of time. The fifth period of time may be shorter or longer than the any one of the first, second, third, or fourth periods of time. In some versions, one or more of steps (1008, 1012, 1018, 1022, 1026) may have a duration ranging from approximately 30 seconds to approximately 300 seconds.

At step (1028), the method shown in plot (1000) includes venting sterilization chamber (152) to increase the pressure within sterilization chamber (152) to a sixth pressure, shown as atmospheric pressure (ATM). While not shown, in some instances the sixth pressure may be approximately 5 torr to approximately 30 torr greater than the fifth pressure, and in some instances the sixth pressure may be between approximately 10 torr to approximately 15 torr greater than the fifth pressure.

While method steps (1002, 1004, 1006, 1008, 1010, 1012, 1014, 1016, 1018, 1020, 1022, 1024, 1026, 1028) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1000), in the middle of the method shown in plot (1000), and after completing the method shown in plot (1000). For example, variations may include one or more steps before or after vacuum step (1004) or one or more steps before or after venting steps (1010, 1020, 1024, 1028).

G. Sixth Exemplary Alternative Sterilization Cycle

Figure 11:
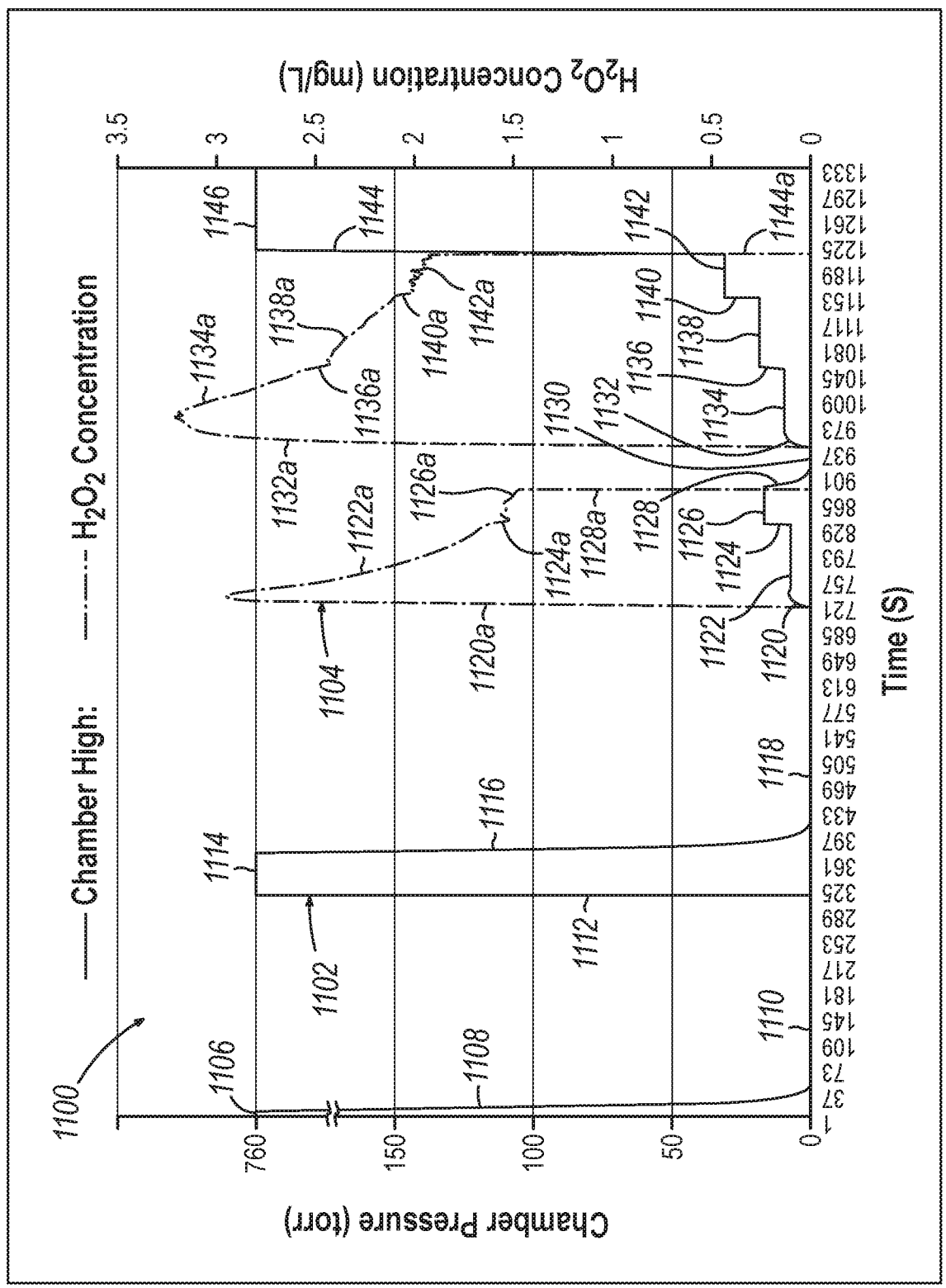
FIG. 11 depicts a graph showing a seventh exemplary plot of the pressure in a sterilization chamber of the sterilizing cabinet of FIG. 1 over time, laid over an exemplary plot of the hydrogen peroxide concentration in the sterilization chamber of the sterilizing cabinet of FIG. 1 over time during performance of a sixth exemplary alternative sterilization cycle.

FIG. 11 depicts a graph showing a seventh exemplary plot (1100) of the pressure in sterilization chamber (152) of sterilizing cabinet (150) of FIG. 1 over time overlaid a graph showing the hydrogen peroxide concentration in sterilization chamber (152) of sterilizing cabinet (150) of FIG. 1 over time during performance of a sixth exemplary sterilization cycle. FIG. 11 includes both a solid line (1102) showing the pressure of sterilization chamber (152) measured with respect to time in seconds and a dash-dot line (1104) showing the $H_2O_2$ concentration of sterilization chamber (152) measured with respect to time in seconds. These two plots are superimposed over one another with respect to time, which is shown on the horizontal axis. As described above, the sterilization cycle method associated with FIG. 11 may be performed on an endoscope or any other kind of article.

Steps (1106, 1108, 1110, 1112, 1114) include a preinitiation sequence. At step (1106), the method shown in plot (1100) includes receiving the endoscope in sterilization chamber. Alternatively, the endoscope may be received within sterilization chamber (152) at step (1114). For example, at step (1106), the pressure is shown at approximately 760 torr, which equals one atmosphere. At step (1108), the method shown in plot (1100) includes applying a vacuum to sterilization chamber (152) to reduce the pressure within sterilization chamber (152) to a first pressure. It is desirable that the first pressure be less than 100 torr. For example, a vacuum may be applied to sterilization chamber (152) to reduce the pressure to approximately 0 torr to approximately 5 torr. At step (1110), the method shown in plot (1100) includes maintaining the first pressure in sterilization chamber (152) for a first period of time. For example, during at least part of step (1110), plasma may be applied as described above. It may be desirable that the pressure be below 5 torr for the plasma to light. At step (1112), the method shown in plot (1100) includes venting sterilization chamber (152) to increase the pressure to a second pressure, shown as approximately 200 torr. However, other pressures are also envisioned, including higher pressures, such as atmospheric pressure (not shown). At step (1114), the method shown in plot (1100) includes maintaining the pressure in sterilization chamber (152) for a second period of time. As previously described, the endoscope may be received within sterilization chamber (152) during step (1114), where the pressure is at approximately 760 torr (atmospheric pressure).

At step (1116), the method shown in plot (1100) includes applying a vacuum to sterilization chamber (152) to reduce the pressure within sterilization chamber (152) to a third pressure. It is desirable that the third pressure is less than 100 torr. At or below 100 torr, condensation is prevented without the need to either heat sterilization chamber (152) or the gas that introduced during the venting step(s). As shown, vacuum may be applied to sterilization chamber (152) to reduce the pressure to approximately 0 torr to approximately 5 torr. As shown, starting at approximately 383 seconds, the pump activates ("pump down") to create the vacuum. The x-axis shows elapsed time in seconds (S). At step (1118), the method shown in plot (1100) includes maintaining the third pressure in sterilization chamber (152) for a third period of time. For example, during at least part of step (1118), plasma may be applied as described above. It may be desirable that the pressure be below 5 torr for the plasma to light.

At step (1120), the method shown in plot (1100) includes introducing a sterilant into sterilization chamber (152). As shown in FIG. 11, the sterilant is hydrogen peroxide ($H_2O_2$). As shown in step (1120a), the $H_2O_2$ concentration increases to approximately 3 milligrams/liter (mg/L). As shown in step (1120a), sterilant is introduced from approximately 728 seconds to approximately 732 seconds. At step (1122), the method shown in plot (1100) includes maintaining the third pressure in sterilization chamber (152) for a fourth period of time, such that the third pressure is the pressure level stays substantially constant as described above for the third period of time (pre-sterilant application) and for the fourth period of time (post-sterilant application). As shown in step (1122a), the $H_2O_2$ concentration decreases in a non-linear manner; however, other linear and non-linear reductions in $H_2O_2$ concentration are also envisioned. The fourth period of time may be shorter or longer than the any one of the first, second, or third periods of time. As shown, the sterilant and the third pressure of approximately 7 torr may be held to approximately 840 seconds.

At step (1124), the method shown in plot (1100) includes venting sterilization chamber (152) to increase the pressure within sterilization chamber (152) to a fourth pressure. The fourth pressure is greater than the third pressure but is still less than 100 torr. Once again, at or below 100 torr, condensation is prevented without the need to either heat sterilization chamber (152) or the gas that introduced during the venting step(s). For example, in some instances the fourth pressure may be approximately 5 torr to approximately 30 torr greater than the third pressure, and in some instances the fourth pressure may be between approximately 10 torr to approximately 15 torr greater than the third pressure. As shown, sterilization chamber (152) may be vented to approximately 16 torr until 900 seconds. As shown in step (1124a), the $H_2O_2$ concentration decreases while venting. While not shown, this cycle (minus the optional plasma) may be repeated. At step (1126), the method shown in plot (1100) includes maintaining the fourth pressure in sterilization chamber (152) for a fifth period of time. The fifth period of time may be shorter or longer than the any one of the first, second, third, or fourth periods of time. As shown in step (1126a), the $H_2O_2$ concentration decreases in a non-linear manner; however, other linear and non-linear reductions in $H_2O_2$ concentration are also envisioned.

At step (1128), the method shown in plot (1100) includes applying a vacuum to sterilization chamber (152) to reduce the pressure within sterilization chamber (152) to a fifth pressure. As shown, vacuum is applied to the chamber to reduce the pressure to approximately 0 torr to approximately 5 torr. As shown, pump down occurs at approximately 0 torr from approximately 900 seconds to approximately 955 seconds to reduce the pressure within sterilization chamber (152). As shown in step (1128a), the $H_2O_2$ concentration decreases with the vacuum being applied. At step (1130), the method shown in plot (1100) includes maintaining the fifth pressure in sterilization chamber (152) for a sixth period of time. The sixth period of time may be shorter or longer than the any one of the first, second, third, fourth, or fifth periods of time.

At step (1132), the method shown in plot (1100) includes introducing additional sterilant into sterilization chamber (152). The same or different sterilant may be used from step (1120). As shown in step (1132a), $H_2O_2$ is introduced from approximately 955 to 1000 seconds, which causes the pressure to rise to approximately 5 torr to approximately 10 torr. At step (1134), the method shown in plot (1100) includes maintaining the fifth pressure in sterilization chamber (152) for a seventh period of time. Sterilant (shown as $H_2O_2$) of a pressure of approximately 10 torr held to approximately 1060 seconds. The seventh period of time may be shorter or longer than the any one of the first, second, third, fourth, fifth, or sixth periods of time. As shown in step (1134a), the $H_2O_2$ concentration decreases in a non-linear manner; however, other linear and non-linear reductions in $H_2O_2$ concentration are also envisioned.

At step (1136), the method shown in plot (1100) includes venting sterilization chamber (152) to increase the pressure within sterilization chamber (152) to a sixth pressure. The sixth pressure is greater than the fifth pressure but is still less than 100 torr. As described below, stepwise venting is shown three times; however, greater or fewer occurrences of stepwise venting is also envisioned. For example, in some instances the sixth pressure may be approximately 5 torr to approximately 30 torr greater than the fifth pressure, and in some instances the sixth pressure may be between approximately 10 torr to approximately 15 torr greater than the fifth pressure. The sixth pressure may be greater than or less than the fourth pressure at step (1126). As shown, the first vent is to approximately 20 torr and is held to 1160 seconds. As shown in step (1136a), the $H_2O_2$ concentration decreases while venting. At step (1138), the method shown in plot (1100) includes maintaining the sixth pressure in sterilization chamber (152) for an eighth period of time. The eighth period of time may be shorter or longer than the any one of the first, second, third, fourth, fifth, sixth of seventh periods of time. As shown in step (1138a), the $H_2O_2$ concentration decreases in a non-linear manner; however, other linear and non-linear reductions in $H_2O_2$ concentration are also envisioned.

At step (1140), the method shown in plot (1100) includes venting sterilization chamber (152) to increase the pressure within sterilization chamber (152) to a seventh pressure. The seventh pressure is greater than the sixth pressure but is still less than 100 torr. For example, in some instances the seventh pressure may be approximately 5 torr to approximately 30 torr greater than the sixth pressure, and in some instances the seventh pressure may be between approximately 10 torr to approximately 15 torr greater than the sixth pressure. The seventh pressure may be greater than or less than the fourth pressure at step (1126). The second vent is to 30 torr and held to 1225 seconds. As shown in step (1140a), the $H_2O_2$ concentration decreases while venting. At step (1142), the method shown in plot (1100) includes maintaining the seventh pressure in sterilization chamber (152) for a ninth period of time. The ninth period of time may be shorter or longer than the any one of the first, second, third, fourth, fifth, sixth, seventh or eighth periods of time.

At step (1144), the method shown in plot (1100) includes venting sterilization chamber (152) to increase the pressure within sterilization chamber (152) to an eighth pressure, which may be atmospheric pressure (ATM). The eighth pressure is greater than the seventh pressure but is still less than 100 torr. For example, in some instances the eighth pressure may be approximately 5 torr to approximately 30 torr greater than the seventh pressure, and in some instances the eighth pressure may be between approximately 10 torr to approximately 15 torr greater than the seventh pressure. As shown, the vent is to atmospheric pressure and held to 1333 seconds. As shown in step (1144a), the $H_2O_2$ concentration decreases while venting. At step (1146), the method shown in plot (1100) includes maintaining the eighth pressure in sterilization chamber (152) for a tenth period of time. The tenth period of time may be shorter or longer than the any one of the first, second, third, fourth, fifth, sixth, seventh, eighth, or ninth periods of time. In some versions, one or more of steps (1110, 1114, 1118, 1122, 1126, 1130, 1134, 1138, 1142, 1146) may have a duration ranging from between approximately 30 seconds to approximately 300 seconds.

While method steps (1106, 1108, 1110, 1112, 1114, 1116, 1118, 1120, 1122, 1124, 1126, 1128, 1130, 1132, 1134, 1136, 1138, 1140, 1142, 1144, 1146) are shown in numerically increasing sequential order with each prior step terminating into the beginning of the next successive step, variations are also envisioned. Pulses may cause agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1100), in the middle of the method shown in plot (1100), and after completing the method shown in plot (1100). For example, pump down to 0 torr and entire cycle (including steps (1116-1146)) may be repeated. For example, variations may include one or more steps before or after vacuum steps (1108, 1116, 1128) or one or more steps before or after venting steps (1124, 1136, 1140, 1144). Further stepwise venting may optionally occur, until atmospheric pressure (ATM) is reached in sterilization chamber (152).

H. Seventh Exemplary Alternative Sterilization Cycle

Figure 12:
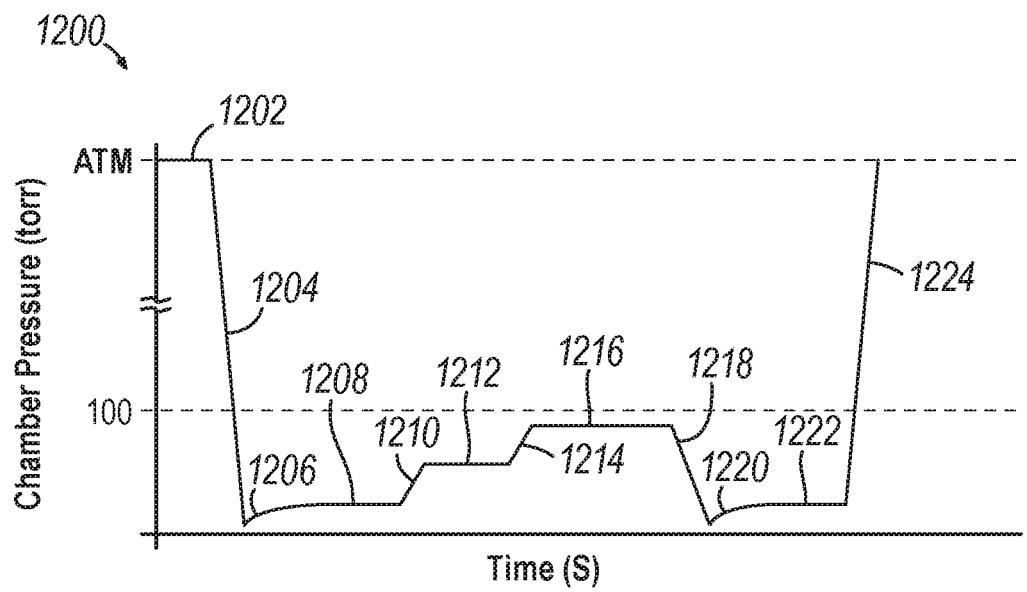
FIG. 12 depicts a graph showing an eighth exemplary plot of the pressure in a sterilization chamber of the sterilizing cabinet of FIG. 1 over time during performance of a seventh exemplary alternative sterilization cycle.

FIG. 12 depicts a graph showing an eighth exemplary plot (1200) of the pressure in sterilization chamber (152) of sterilizing cabinet (150) of FIG. 1 over time during performance of a seventh exemplary alternative sterilization cycle. As described above, the sterilization cycle method associated with FIG. 12 may be performed on an endoscope or any other kind of article.

At step (1202), the method shown in plot (1200) includes receiving the endoscope in sterilization chamber. At step (1204), the method shown in plot (1200) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1206), the method shown in plot (1200) includes introducing a sterilant into sterilization chamber (152). At step (1208), the method shown in plot (1200) includes maintaining the first pressure in sterilization chamber (152) for a first period of time.

At step (1210), the method shown in plot (1200) includes venting sterilization chamber (152) to increase the pressure within sterilization chamber (152) to a second pressure. The second pressure is greater than the first pressure but is still less than 100 torr. Once again, at or below 100 torr, condensation is prevented without the need to either heat sterilization chamber (152) or the gas that introduced during the venting step(s). For example, in some instances the second pressure may be approximately 5 torr to approximately 30 torr greater than the first pressure, and in some instances the second pressure may be between approximately 10 torr to approximately 15 torr greater than the first pressure. At step (1212), the method shown in plot (1200) includes maintaining the second pressure in sterilization chamber (152) for a second period of time. The second period of time may be shorter or longer than the first period of time.

At step (1214), the method shown in plot (1200) includes venting sterilization chamber (152) to increase the pressure within sterilization chamber (152) to a third pressure. For example, in some instances the third pressure may be approximately 5 torr to approximately 30 torr greater than the second pressure, and in some instances the third pressure may be between approximately 10 torr to approximately 15 torr greater than the second pressure. At step (1216), the method shown in plot (1200) includes maintaining the third pressure in sterilization chamber (152) for a third period of time. The third period of time may be shorter or longer than any one of the first or second periods of time.

At step (1218), the method shown in plot (1200) includes applying a vacuum to sterilization chamber (152) to reduce the pressure within sterilization chamber (152) to a fourth pressure. The fourth pressure is less than 100 torr. For example, vacuum may be applied to sterilization chamber (152) to reduce the pressure to approximately 0 torr to approximately 5 torr. At step (1220), the method shown in plot (1200) includes introducing additional sterilant into sterilization chamber (152). The same sterilant or a different sterilant that was used in step (1206) may be used. At step (1222), the method shown in plot (1200) includes maintaining the fourth pressure in sterilization chamber (152) for a fourth period of time. The fourth period of time may be shorter or longer than any one of the first, second, or third periods of time. In some versions, one or more of steps (1208, 1212, 1216, 1222) may have a duration ranging from approximately 30 seconds to approximately 300 seconds.

At step (1224), the method shown in plot (1200) includes venting sterilization chamber (152) to increase the pressure within sterilization chamber (152) to a fifth pressure, shown as atmospheric pressure (ATM). While not shown, in some instances the fifth pressure may be approximately 5 torr to approximately 30 torr greater than the fourth pressure, and in some instances the fifth pressure may be between approximately 10 torr to approximately 15 torr greater than the fourth pressure. While not shown, prior to reaching atmospheric pressure (ATM), venting and maintaining steps may be performed and in some instances may be repeated (e.g., once, twice, or three or more times).

While method steps (1202, 1204, 1206, 1208, 1210, 1212, 1214, 1216, 1218, 1220, 1222, 1224) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1200), in the middle of the method shown in plot (1200), and after completing the method shown in plot (1200). For example, variations may include one or more steps before or after vacuum steps (1204, 1218) or one or more steps before or after venting steps (1210, 1214, 1224).

I. Eighth Exemplary Alternative Sterilization Cycle

Figure 13:
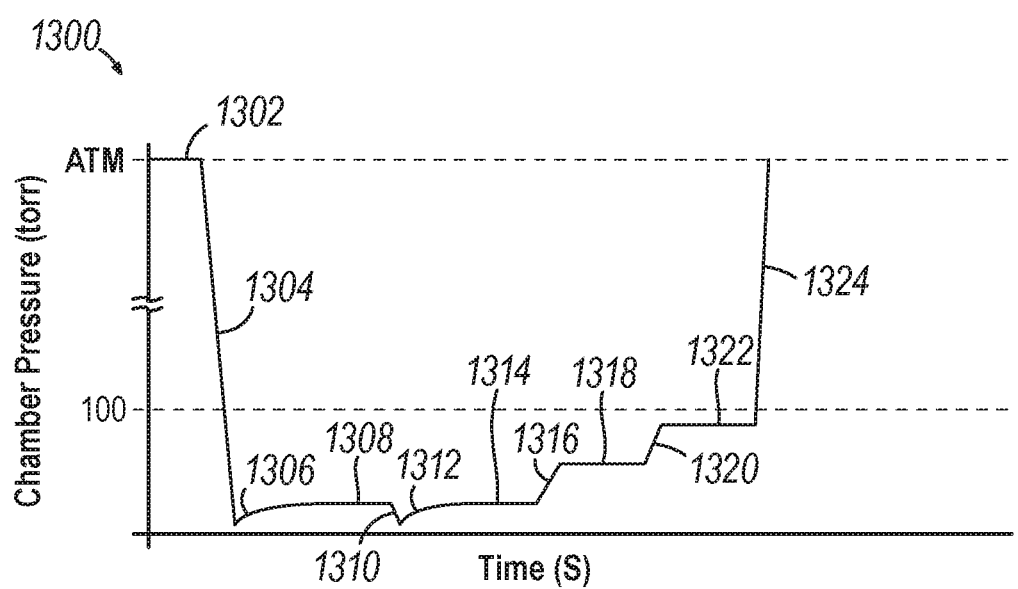
FIG. 13 depicts a graph showing a ninth exemplary plot of the pressure in a sterilization chamber of the sterilizing cabinet of FIG. 1 over time during performance of an eighth exemplary alternative sterilization cycle.

FIG. 13 depicts a graph showing a ninth exemplary plot (1300) of the pressure in sterilization chamber (152) of sterilizing cabinet (150) of FIG. 1 over time during performance of an eighth exemplary sterilization cycle. As described above, the sterilization cycle method associated with FIG. 13 may be performed on an endoscope or any other kind of article.

At step (1302), the method shown in plot (1300) includes receiving the endoscope in sterilization chamber (152). At step (1304), the method shown in plot (1300) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1306), the method shown in plot (1300) includes introducing a sterilant into sterilization chamber (152). At step (1308), the method shown in plot (1300) includes maintaining the first pressure in sterilization chamber (152) for a first period of time.

At step (1310), the method shown in plot (1300) includes applying a vacuum to sterilization chamber (152) to reduce the pressure within sterilization chamber (152) to a second pressure. The second pressure is less than 100 torr. Once again, at or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. The second pressure may be greater than or less than the first pressure. At step (1312), the method shown in plot (1300) includes introducing additional sterilant into sterilization chamber (152). The same or different sterilant may be used compared to step (1306). At step (1314), the method shown in plot (1300) includes maintaining the second pressure in sterilization chamber (152) for a second period of time. The second period of time may be shorter or longer than the first period of time.

At step (1316), the method shown in plot (1300) includes venting sterilization chamber (152) to increase the pressure within sterilization chamber (152) to a third pressure. The third pressure is greater than the second pressure but is still less than 100 torr. For example, in some instances the third pressure may be approximately 5 torr to approximately 30 torr greater than the second pressure, and in some instances the third pressure may be between approximately 10 torr to approximately 30 torr greater than the second pressure. At step (1318), the method shown in plot (1300) includes maintaining the third pressure in sterilization chamber (152) for a third period of time. The third period of time may be shorter or longer than the first or second periods of time.

At step (1320), the method shown in plot (1300) includes venting sterilization chamber (152) to increase the pressure within sterilization chamber (152) to a fourth pressure. For example, in some instances the fourth pressure may be approximately 5 torr to approximately 30 torr greater than the third pressure, and in some instances the fourth pressure may be between approximately 10 torr to approximately 30 torr greater than the third pressure. At step (1322), the method shown in plot (1300) includes maintaining the fourth pressure in sterilization chamber (152) for a fourth period of time. The fourth period of time may be shorter or longer than any one of the first, second, or third periods of time. In some versions, one or more of steps (1308, 1314, 1318, 1322) may have a duration ranging from approximately 30 seconds to approximately 300 seconds.

At step (1324), the method shown in plot (1300) includes venting sterilization chamber (152) to increase the pressure within sterilization chamber (152) to a fifth pressure, shown as atmospheric pressure (ATM). Prior to reaching atmospheric pressure (ATM), additional venting and maintaining steps similar to steps (1316, 1318, 1320, 1322) may be performed and in some instances may be repeated (e.g., once, twice, or three or more times). While not shown, in some instances the fifth pressure may be approximately 5 torr to approximately 30 torr greater than the fourth pressure, and in some instances the fifth pressure may be between approximately 10 torr to approximately 15 torr greater than the fourth pressure.

While method steps (1302, 1304, 1306, 1308, 1310, 1312, 1314, 1316, 1318, 1320, 1322, 1324) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1300), in the middle of the method shown in plot (1300), and after completing the method shown in plot (1300). For example, variations may include one or more steps before or after vacuum steps (1304, 1310) or one or more steps before or after venting steps (1316, 1320, 1324).

J. Ninth Exemplary Alternative Sterilization Cycle

Figure 14:
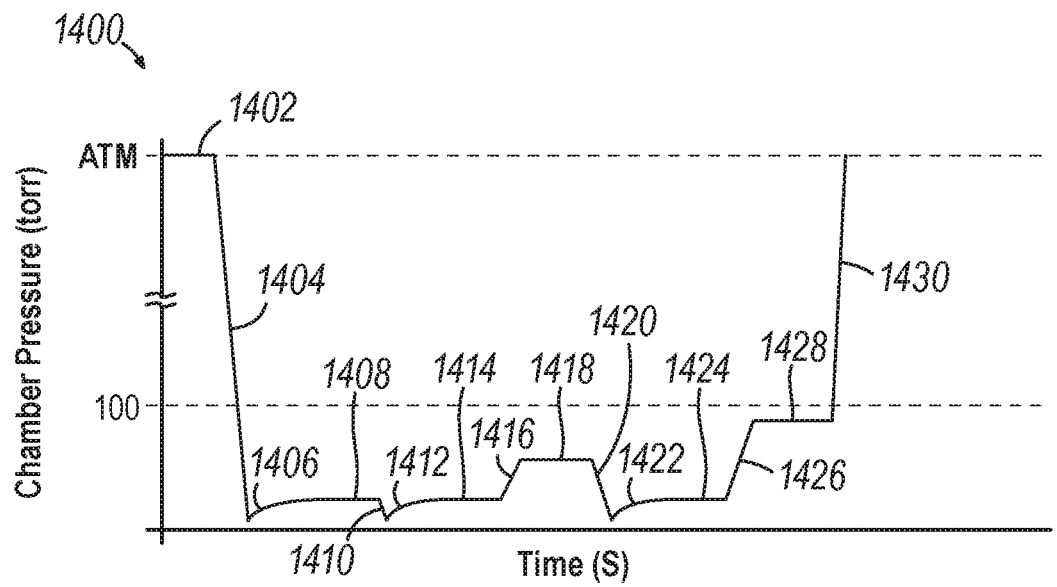
FIG. 14 depicts a graph showing a tenth exemplary plot of the pressure in a sterilization chamber of the sterilizing cabinet of FIG. 1 over time during performance of a ninth exemplary alternative sterilization cycle.

FIG. 14 depicts a graph showing a tenth exemplary plot (1400) of the pressure in sterilization chamber (152) of the sterilizing cabinet (150) of FIG. 1 over time during performance of a ninth exemplary sterilization cycle. As described above, the sterilization cycle method associated with FIG. 14 may be performed on an endoscope or any other kind of article.

At step (1402), the method shown in plot (1400) includes receiving the endoscope in sterilization chamber (152). At step (1404), the method shown in plot (1400) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1406), the method shown in plot (1400) includes introducing a sterilant into sterilization chamber (152). At step (1408), the method shown in plot (1400) includes maintaining the first pressure in sterilization chamber (152) for a first period of time.

At step (1410), the method shown in plot (1400) includes applying a vacuum to sterilization chamber (152) to reduce the pressure within sterilization chamber (152) to a second pressure. The second pressure is less than 100 torr. Once again, at or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1412), the method shown in plot (1400) includes introducing additional sterilant into sterilization chamber (152). The same or different sterilant may be used compared to step (1406). At step (1414), the method shown in plot (1400) includes maintaining the second pressure in sterilization chamber (152) for a second period of time. The second period of time may be shorter or longer than the first period of time.

At step (1416), the method shown in plot (1400) includes venting sterilization chamber (152) to increase the pressure within sterilization chamber (152) to a third pressure. The third pressure is greater than the second pressure but is still less than 100 torr. For example, in some instances the third pressure may be approximately 5 torr to approximately 30 torr greater than the second pressure, and in some instances the third pressure may be between approximately 10 torr to approximately 15 torr greater than the second pressure. At step (1418), the method shown in plot (1400) includes maintaining the third pressure in sterilization chamber (152) for a third period of time. The third period of time may be shorter or longer than the second period of time.

At step (1420), the method shown in plot (1400) includes applying a vacuum to sterilization chamber (152) to reduce the pressure within sterilization chamber (152) to a fourth pressure. The fourth pressure is less than 100 torr. For example, vacuum may be applied to sterilization chamber (152) to reduce the pressure to approximately 0 torr to approximately 5 torr. The fourth pressure may be greater than or less than the first and second pressures. At step (1422), the method shown in plot (1400) includes introducing a sterilant into sterilization chamber (152). The same or different sterilant may be used compared to step (1406) or (1412). At step (1424), the method shown in plot (1400) includes maintaining the fourth pressure in sterilization chamber (152) for a fourth period of time. The fourth period of time may be shorter or longer than the first, second, or third periods of time.

At step (1426), the method shown in plot (1400) includes venting sterilization chamber (152) to increase the pressure within sterilization chamber (152) to a fifth pressure. For example, in some instances the fifth pressure may be approximately 5 torr to approximately 30 torr greater than the fourth pressure, and in some instances the fifth pressure may be between approximately 10 torr to approximately 15 torr greater than the fourth pressure. At step (1428), the method shown in plot (1400) includes maintaining the fifth pressure in sterilization chamber (152) for a fifth period of time. In some versions, one or more of steps (1408, 1414, 1418, 1424, 1428) may have a duration ranging from approximately 30 seconds to approximately 300 seconds.

At step (1430), the method shown in plot (1400) includes venting sterilization chamber (152) to increase the pressure within sterilization chamber (152) to a sixth pressure, shown as atmospheric pressure (ATM). While not shown, venting step (1426) and maintaining step (1428) may be repeated (e.g., once, twice, or three or more times). While not shown, in some instances the sixth pressure may be approximately 5 torr to approximately 30 torr greater than the fifth pressure, and in some instances the sixth pressure may be between approximately 10 torr to approximately 15 torr greater than the fifth pressure.

While method steps (1402, 1404, 1406, 1408, 1410, 1412, 1414, 1416, 1418, 1420, 1422, 1424, 1426, 1428, 1430) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1400), in the middle of the method shown in plot (1400), and after completing the method shown in plot (1400). For example, variations may include one or more steps before or after vacuum steps (1404, 1410, 1420) or one or more steps before or after venting steps (1416, 1426, 1430).

K. Tenth Exemplary Alternative Sterilization Cycle

Figure 15:
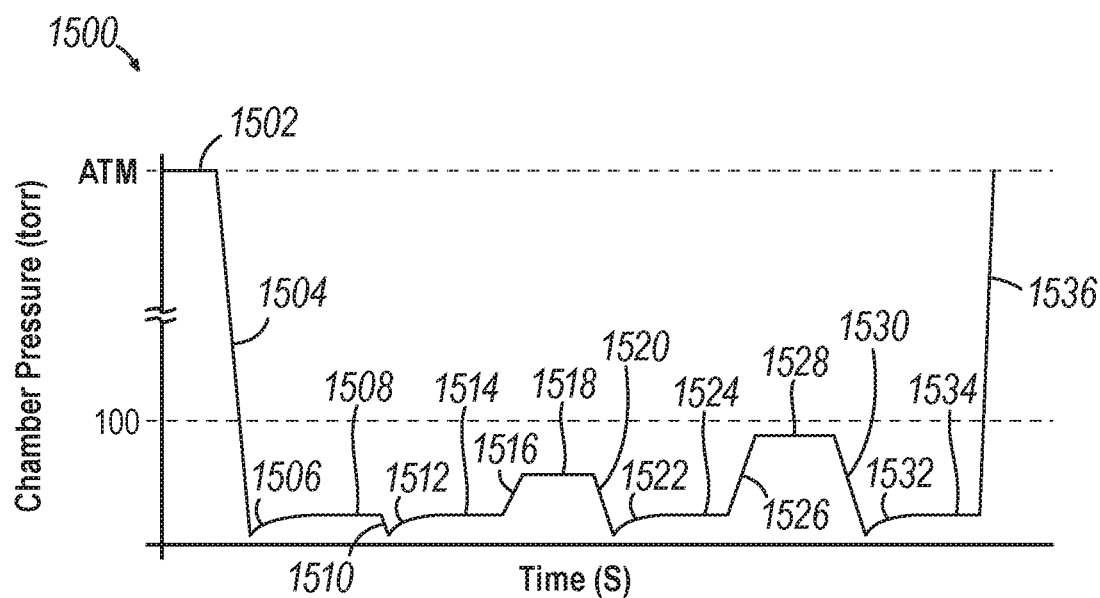
FIG. 15 depicts a graph showing an eleventh exemplary plot of the pressure in a sterilization chamber of the sterilizing cabinet of FIG. 1 over time during performance of a tenth exemplary alternative sterilization cycle.

FIG. 15 depicts a graph showing an eleventh exemplary plot (1500) of the pressure in sterilization chamber (152) of sterilizing cabinet (150) of FIG. 1 over time during performance of a tenth exemplary sterilization cycle. As described above, the sterilization cycle method associated with FIG. 15 may be performed on an endoscope or any other kind of article.

At step (1502), the method shown in plot (1500) includes receiving the endoscope in sterilization chamber (152). At step (1504), the method shown in plot (1500) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to the chamber to reduce the pressure to approximately 0 torr to approximately 5 torr. At step (1506), the method shown in plot (1500) includes introducing a sterilant into sterilization chamber (152). At step (1508), the method shown in plot (1500) includes maintaining the first pressure in sterilization chamber (152) for a first period of time.

At step (1510), the method shown in plot (1500) includes applying a vacuum to sterilization chamber (152) to reduce the pressure within sterilization chamber (152) to a second pressure. The second pressure is less than 100 torr. Once again, at or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1512), the method shown in plot (1500) includes introducing additional sterilant into sterilization chamber (152). The sterilant may be the same or different than the sterilant introduced in step (1506). At step (1514), the method shown in plot (1500) includes maintaining the second pressure in sterilization chamber (152) for a second period of time. The second period of time may be shorter or longer than the first period of time.

At step (1516), the method shown in plot (1500) includes venting sterilization chamber (152) to increase the pressure within sterilization chamber (152) to a third pressure. The third pressure is greater than the second pressure but is still less than 100 torr. For example, in some instances the third pressure may be approximately 5 torr to approximately 30 torr greater than the second pressure, and in some instances the third pressure may be between approximately 10 torr to approximately 15 torr greater than the second pressure. At step (1518), the method shown in plot (1500) includes maintaining the third pressure in sterilization chamber (152) for a third period of time. The third period of time may be shorter or longer than the first or second periods of time.

At step (1520), the method shown in plot (1500) includes applying a vacuum to sterilization chamber (152) to reduce the pressure within sterilization chamber (152) to a fourth pressure. The fourth pressure is less than 100 torr. For example, vacuum may be applied to sterilization chamber (152) to reduce the pressure within sterilization chamber (152) to approximately 0 torr to approximately 5 torr. At step (1522), the method shown in plot (1500) includes introducing a sterilant into sterilization chamber (152). The sterilant may be the same or different than the sterilant introduced in step (1506) or (1512). At step (1524), the method shown in plot (1500) includes maintaining the fourth pressure in sterilization chamber (152) for a fourth period of time. The fourth period of time may be shorter or longer than any one of the first, second, or third periods of time.

At step (1526), the method shown in plot (1500) includes venting sterilization chamber (152) to increase the pressure within sterilization chamber (152) to a fifth pressure. For example, in some instances the fifth pressure may be approximately 5 torr to approximately 30 torr greater than the fourth pressure, and in some instances the fifth pressure may be between approximately 10 torr to approximately 15 torr greater than the fourth pressure. At step (1528), the method shown in plot (1500) includes maintaining the fifth pressure in sterilization chamber (152) for a fifth period of time. The fifth period of time may be shorter or longer than any one of the first, second, third, or fourth periods of time.

At step (1530), the method shown in plot (1500) includes applying a vacuum to sterilization chamber (152) to reduce the pressure within sterilization chamber (152) to a sixth pressure. The sixth pressure is less than 100 torr. For example, vacuum may be applied to sterilization chamber (152) to reduce the pressure to approximately 0 torr to approximately 5 torr. At step (1532), the method shown in plot (1500) includes introducing additional sterilant into sterilization chamber (152). The sterilant may be the same or different than the sterilant introduced in steps (1506), (1512), or (1522). At step (1534), the method shown in plot (1500) includes maintaining the sixth pressure in sterilization chamber (152) for a sixth period of time. The sixth period of time may be shorter or longer than any one of the first, second, third, fourth, or fifth periods of time. In some versions, one or more of steps (1508, 1514, 1518, 1524, 1528, 1534) may have a duration ranging from approximately 30 seconds to approximately 300 seconds.

At step (1536), the method shown in plot (1500) includes venting sterilization chamber (152) to increase the pressure within sterilization chamber (152) to a seventh pressure, shown as atmospheric pressure (ATM). While not shown, prior to reaching atmospheric pressure (ATM), additional venting and maintaining steps similar to steps (1526, 1528) may be performed and in some instances may be repeated (e.g., once, twice, or three or more times). While not shown, in some instances the seventh pressure may be approximately 5 torr to approximately 30 torr greater than the sixth pressure, and in some instances the seventh pressure may be between approximately 10 torr to approximately 15 torr greater than the sixth pressure.

While method steps (1502, 1504, 1506, 1508, 1510, 1512, 1514, 1516, 1518, 1520, 1522, 1524, 1526, 1528, 1530, 1532, 1534, 1536) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1500), in the middle of the method shown in plot (1500), and after completing the method shown in plot (1500). For example, variations may include one or more steps before or after vacuum steps (1504, 1510, 1520, 1530) or one or more steps before or after venting steps (1516, 1526, 1536).

L. Eleventh Exemplary Alternative Sterilization Cycle

Figure 16:
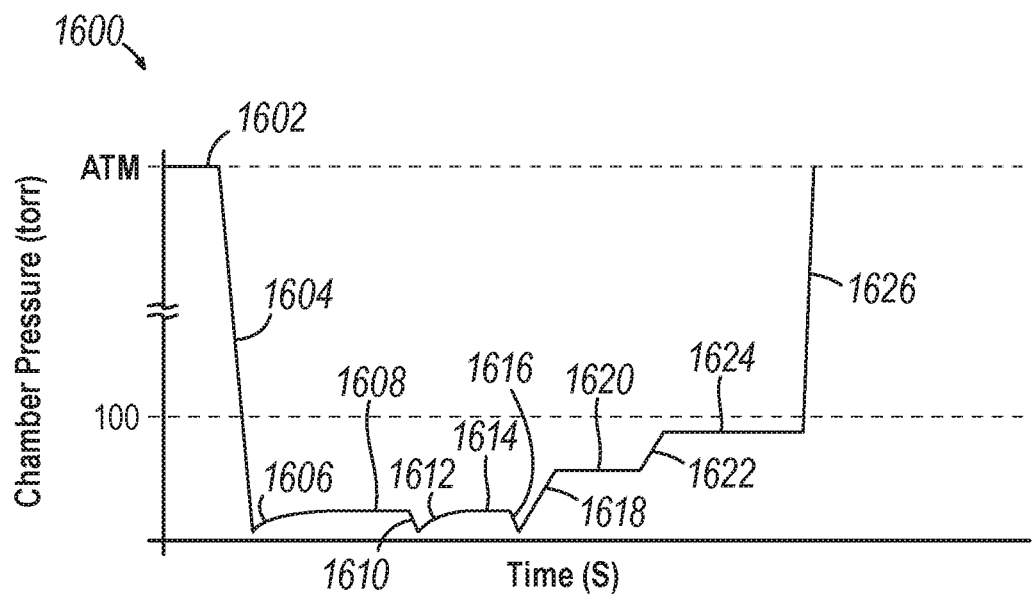
FIG. 16 depicts a graph showing a twelfth exemplary plot of the pressure in a sterilization chamber of the sterilizing cabinet of FIG. 1 over time during performance of an eleventh exemplary sterilization cycle.

FIG. 16 depicts a graph showing a twelfth exemplary plot (1600) of the pressure in sterilization chamber (152) of sterilizing cabinet (150) of FIG. 1 over time during performance of an eleventh exemplary sterilization cycle. As described above, the sterilization cycle method associated with FIG. 16 may be performed on an endoscope or any other kind of article.

At step (1602), the method shown in plot (1600) includes receiving the endoscope in sterilization chamber (152). At step (1604), the method shown in plot (1600) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, the vacuum may be applied to sterilization chamber (152) to reduce the pressure to approximately 0 torr to approximately 5 torr. At step (1606), the method shown in plot (1600) includes introducing a sterilant into sterilization chamber (152). At step (1608), the method shown in plot (1600) includes maintaining the first pressure in sterilization chamber (152) for a first period of time.

At step (1610), the method shown in plot (1600) includes applying a vacuum to sterilization chamber (152) to reduce the pressure within sterilization chamber (152) to a second pressure. The second pressure is less than 100 torr. Once again, at or below 100 torr, condensation is prevented without the need to either heat sterilization chamber (152) or the gas that introduced during the venting step(s). The second pressure may be greater than or less than the first pressure. For example, vacuum may be applied to sterilization chamber (152) to reduce the pressure to approximately 0 torr to approximately 5 torr. At step (1612), the method shown in plot (1600) includes introducing a sterilant into sterilization chamber (152). The sterilant may be the same or different than the sterilant introduced in step (1606). At step (1614), the method shown in plot (1600) includes maintaining the second pressure in sterilization chamber (152) for a second period of time. The second period of time may be shorter or longer than the first period of time.

At step (1616), the method shown in plot (1600) includes applying a vacuum to sterilization chamber (152) to reduce the pressure within sterilization chamber (152) to a third pressure. For example, vacuum may be applied to sterilization chamber (152) to reduce the pressure to approximately 0 torr to approximately 5 torr.

At step (1618), the method shown in plot (1600) includes venting sterilization chamber (152) to increase the pressure within sterilization chamber (152) to a fourth pressure. The fourth pressure is greater than the third pressure but is still less than 100 torr. For example, in some instances the fourth pressure may be approximately 10 torr to 100 torr greater than the third pressure, and in some instances the fourth pressure may be between approximately 10 torr to approximately 30 torr greater than the third pressure. At step (1620), the method shown in plot (1600) includes maintaining the fourth pressure in sterilization chamber (152) for a third period of time. The third period of time may be shorter or longer than any one of the first or second periods of time.

At step (1622), the method shown in plot (1600) includes venting sterilization chamber (152) to increase the pressure within sterilization chamber (152) to a fifth pressure. For example, in some instances the fifth pressure may be approximately 10 torr to 100 torr greater than the fourth pressure, and in some instances the fifth pressure may be between approximately 10 torr to approximately 30 torr greater than the fourth pressure. At step (1624), the method shown in plot (1600) includes maintaining the fifth pressure in sterilization chamber (152) for a fourth period of time. The fourth period of time may be shorter or longer than any one of the first, second, or third periods of time. In some versions, one or more of steps (1608, 1614, 1620, 1624) may have a duration ranging from approximately 30 seconds to approximately 300 seconds.

At step (1626), the method shown in plot (1600) includes venting sterilization chamber (152) to increase the pressure within sterilization chamber (152) to a sixth pressure, shown as atmospheric pressure (ATM). While not shown, in some instances the sixth pressure may be approximately 5 torr to approximately 30 torr greater than the fifth pressure, and in some instances the sixth pressure may be between approximately 10 torr to approximately 15 torr greater than the fifth pressure. Prior to reaching atmospheric pressure (ATM), additional venting and maintaining steps similar to steps (1618, 1620, 1622, 1624) may be performed and in some instances may be repeated (e.g., once, twice, or three or more times).

While method steps (1602, 1604, 1606, 1608, 1610, 1612, 1614, 1616, 1618, 1620, 1622, 1624, 1626) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1600), in the middle of the method shown in plot (1600), and after completing the method shown in plot (1600). For example, variations may include one or more steps before or after vacuum steps (1604, 1610, 1616) or one or more steps before or after venting steps (1618, 1622, 1626).

M. Twelfth Exemplary Alternative Sterilization Cycle

Figure 17:
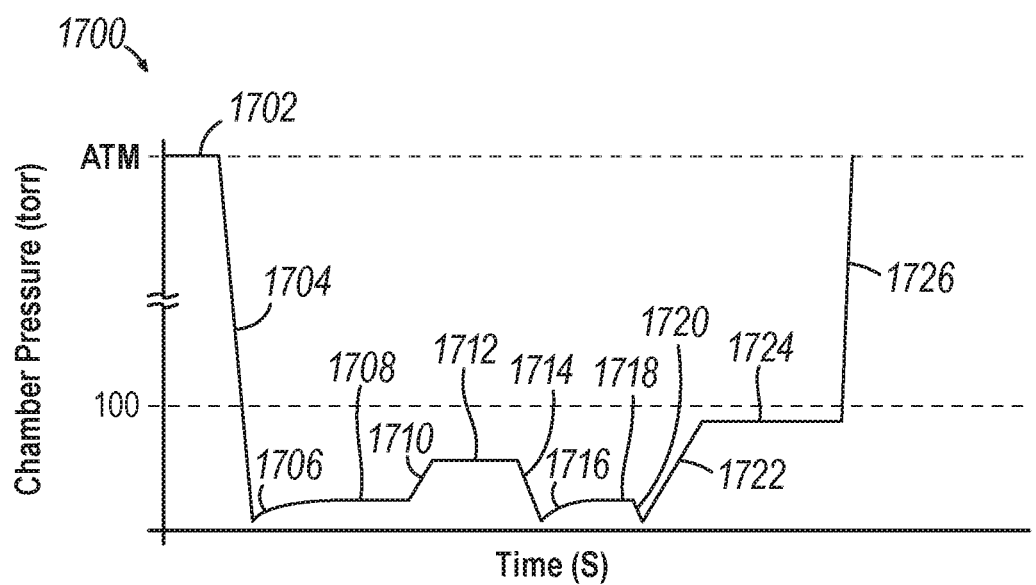
FIG. 17 depicts a graph showing a thirteenth exemplary plot of the pressure in a sterilization chamber of the sterilizing cabinet of FIG. 1 over time during performance of a twelfth exemplary sterilization cycle.

FIG. 17 depicts a graph showing a thirteenth exemplary plot (1700) of the pressure in sterilization chamber (152) of sterilizing cabinet (150) of FIG. 1 over time during performance of a twelfth exemplary sterilization cycle. As described above, the sterilization cycle method associated with FIG. 17 may be performed on an endoscope or any other kind of article.

At step (1702), the method shown in plot (1700) includes receiving the endoscope in sterilization chamber. At step (1704), the method shown in plot (1700) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1706), the method shown in plot (1700) includes introducing a sterilant into sterilization chamber (152). At step (1708), the method shown in plot (1700) includes maintaining the first pressure in sterilization chamber (152) for a first period of time.

At step (1710), the method shown in plot (1700) includes venting sterilization chamber (152) to increase the pressure within sterilization chamber (152) to a second pressure. The second pressure is greater than the first pressure but is still less than 100 torr. Once again, at or below 100 torr, condensation is prevented without the need to either heat sterilization chamber (152) or the gas that introduced during the venting step(s). For example, in some instances the second pressure may be approximately 10 torr to 100 torr greater than the first pressure, and in some instances the second pressure may be between approximately 10 torr to approximately 30 torr greater than the first pressure. At step (1712), the method shown in plot (1700) includes maintaining the second pressure in sterilization chamber (152) for a second period of time. The second period of time may be shorter or longer than the first period of time.

At step (1714), the method shown in plot (1700) includes applying a vacuum to sterilization chamber (152) to reduce the pressure within sterilization chamber (152) to a third pressure. The third pressure is less than 100 torr. For example, vacuum may be applied to sterilization chamber (152) to reduce the pressure to approximately 0 torr to approximately 5 torr. The third pressure may be greater than or less than the first pressure. At step (1716), the method shown in plot (1700) includes introducing additional sterilant into sterilization chamber (152). The sterilant may be the same or different than the sterilant introduced in step (1706). At step (1718), the method shown in plot (1700) includes maintaining the third pressure in sterilization chamber (152) for a third period of time. The third period of time may be shorter or longer than the second period of time.

At step (1720), the method shown in plot (1700) includes applying a vacuum to sterilization chamber (152) to reduce the pressure within sterilization chamber (152) to a fourth pressure. For example, vacuum may be applied to sterilization chamber (152) to reduce the pressure to approximately 0 torr to approximately 5 torr. The fourth pressure may be greater than or less than any one of the first, second, or third pressures.

At step (1722), the method shown in plot (1700) includes venting sterilization chamber (152) to increase the pressure within sterilization chamber (152) to a fifth pressure. The fifth pressure is greater than the fourth pressure but is still less than 100 torr. For example, in some instances the fifth pressure may be approximately 10 torr to 100 torr greater than the fourth pressure, and in some instances the fifth pressure may be between approximately 10 torr to approximately 30 torr greater than the fourth pressure. At step (1724), the method shown in plot (1700) includes maintaining the fifth pressure in sterilization chamber (152) for a fourth period of time. The fourth period of time may be shorter or longer than the second or third periods of time. In some versions, one or more of steps (1708, 1712, 1718, 1724) may have a duration ranging from approximately 30 seconds to approximately 300 seconds.

At step (1726), the method shown in plot (1700) includes venting sterilization chamber (152) to increase the pressure within sterilization chamber (152) to a sixth pressure, shown as atmospheric pressure (ATM). While not shown, prior to reaching atmospheric pressure (ATM), additional venting and maintaining steps similar to steps (1724, 1726) may be performed and in some instances may be repeated (e.g., once, twice, or three or more times). While not shown, in some instances the sixth pressure may be approximately 5 torr to approximately 30 torr greater than the fifth pressure, and in some instances the sixth pressure may be between approximately 10 torr to approximately 15 torr greater than the fifth pressure.

While method steps (1702, 1704, 1706, 1708, 1710, 1712, 1714, 1716, 1718, 1720, 1722, 1724, 1726) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1700), in the middle of the method shown in plot (1700), and after completing the method shown in plot (1700). For example, variations may include one or more steps before or after vacuum steps (1704, 1714, 1720) or one or more steps before or after venting steps (1710, 1722, 1726).

N. Thirteenth Exemplary Alternative Sterilization Cycle

Figure 18:
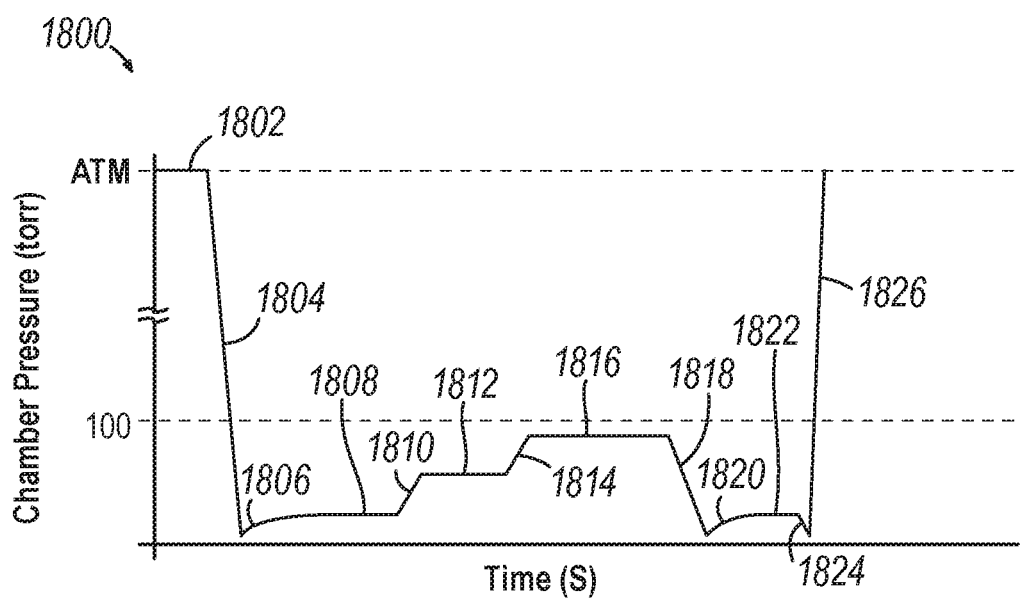
FIG. 18 depicts a graph showing a fourteenth exemplary plot of the pressure in a sterilization chamber of the sterilizing cabinet of FIG. 1 over time during performance of a thirteenth exemplary alternative sterilization cycle.

FIG. 18 depicts a graph showing a fourteenth exemplary plot (1800) of the pressure in sterilization chamber (152) of sterilizing cabinet (150) of FIG. 1 over time during performance of a thirteenth exemplary sterilization cycle. As described above, the sterilization cycle method associated with FIG. 18 may be performed on an endoscope or any other kind of article.

At step (1802), the method shown in plot (1800) includes receiving the endoscope in sterilization chamber (152). At step (1804), the method shown in plot (1800) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1806), the method shown in plot (1800) includes introducing a sterilant into sterilization chamber (152). At step (1808), the method shown in plot (1800) includes maintaining the first pressure in sterilization chamber (152) for a first period of time.

At step (1810), the method shown in plot (1800) includes venting sterilization chamber (152) to increase the pressure within sterilization chamber (152) to a second pressure. The second pressure is greater than the first pressure but is still less than 100 torr. Once again, at or below 100 torr, condensation is prevented without the need to either heat sterilization chamber (152) or the gas that introduced during the venting step(s). For example, in some instances the second pressure may be approximately 10 torr to 100 torr greater than the first pressure, and in some instances the second pressure may be between approximately 10 torr to approximately 30 torr greater than the first pressure.

At step (1812), the method shown in plot (1800) includes maintaining the second pressure in sterilization chamber (152) for a second period of time. The second period of time may be shorter or longer than the first period of time. At step (1814), the method shown in plot (1800) includes venting sterilization chamber (152) to increase the pressure within sterilization chamber (152) to a third pressure. For example, in some instances the third pressure may be approximately 10 torr to 100 torr greater than the second pressure, and in some instances the third pressure may be between approximately 10 torr to approximately 30 torr greater than the second pressure. At step (1816), the method shown in plot (1800) includes maintaining the third pressure in sterilization chamber (152) for a third period of time. The third period of time may be shorter or longer in duration than any one of the first or second periods of time.

At step (1818), the method shown in plot (1800) includes applying a vacuum to sterilization chamber (152) to reduce the pressure within sterilization chamber (152) to a fourth pressure. For example, vacuum may be applied to sterilization chamber (152) to reduce the pressure to approximately 0 torr to approximately 5 torr. The fourth pressure is less than the third pressure. At step (1820), the method shown in plot (1800) includes introducing a sterilant into sterilization chamber (152). The sterilant may be the same or different than the sterilant introduced in step (1806). At step (1822), the method shown in plot (1800) includes maintaining the fourth pressure in sterilization chamber (152) for a fourth period of time. The fourth period of time may be shorter or longer than any one of the first, second or third periods of time. In some versions, one or more of steps (1808, 1812, 1816, 1822) may have a duration ranging from approximately 30 seconds to approximately 300 seconds.

At step (1824), the method shown in plot (1800) includes applying a vacuum to sterilization chamber (152) to reduce the pressure within sterilization chamber (152) to a fifth pressure. The fifth pressure is less than 100 torr. For example, vacuum may be applied to sterilization chamber (152) to reduce the pressure to approximately 0 torr to approximately 5 torr. At step (1826), the method shown in plot (1800) includes venting sterilization chamber (152) to increase the pressure within sterilization chamber (152) to a sixth pressure, shown as atmospheric pressure (ATM). While not shown, in some instances the sixth pressure may be approximately 5 torr to approximately 30 torr greater than the fifth pressure, and in some instances the sixth pressure may be between approximately 10 torr to approximately 15 torr greater than the fifth pressure. While not shown, prior to reaching atmospheric pressure (ATM), additional venting and maintaining steps similar to steps (1814, 1816) may be performed and in some instances may be repeated (e.g., once, twice, or three or more times).

While method steps (1802, 1804, 1806, 1808, 1810, 1812, 1814, 1816, 1818, 1820, 1822, 1824, 1826) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1800), in the middle of the method shown in plot (1800), and after completing the method shown in plot (1800). For example, variations may include one or more steps before or after vacuum steps (1804, 1818, 1824) or one or more steps before or after venting steps (1810, 1814, 1826).

O. Fourteenth Exemplary Alternative Sterilization Cycle

Figure 19:
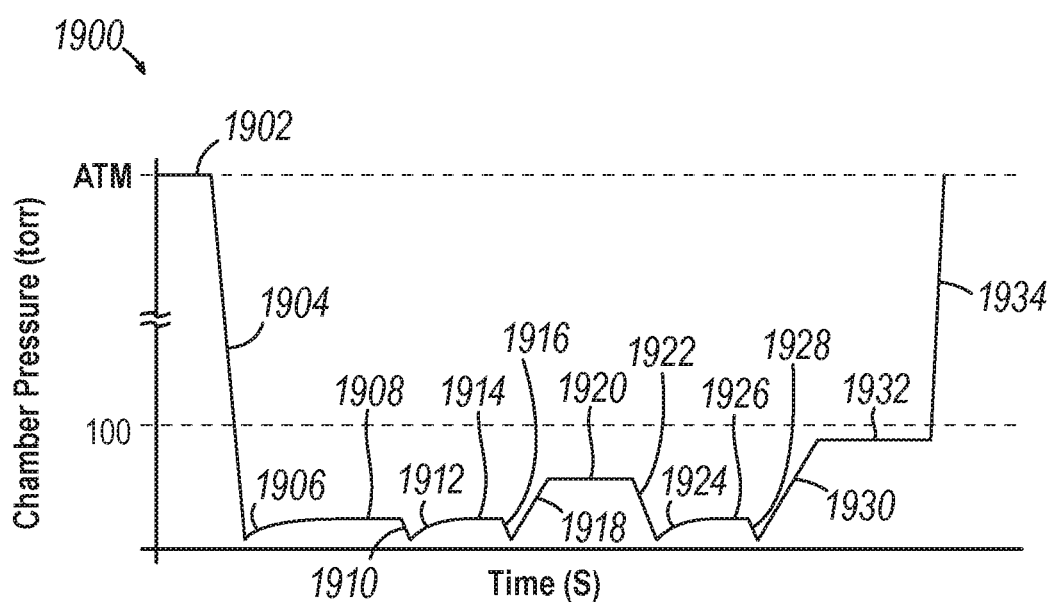
FIG. 19 depicts a graph showing a fifteenth exemplary plot of the pressure in a sterilization chamber of the sterilizing cabinet of FIG. 1 over time during performance of a fourteenth exemplary alternative sterilization cycle.

FIG. 19 depicts a graph showing a fifteenth exemplary plot (1900) of the pressure in sterilization chamber (152) of sterilizing cabinet (150) of FIG. 1 over time during performance of a fourteenth exemplary sterilization cycle. As described above, the sterilization cycle method associated with FIG. 19 may be performed on an endoscope or any other kind of article.

At step (1902), the method shown in plot (1900) includes receiving the endoscope in sterilization chamber (152). At step (1904), the method shown in plot (1900) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1906), the method shown in plot (1900) includes introducing a sterilant into sterilization chamber (152). At step (1908), the method shown in plot (1900) includes maintaining the first pressure in sterilization chamber (152) for a first period of time.

At step (1910), the method shown in plot (1900) includes applying a vacuum to sterilization chamber (152) to reduce the pressure within sterilization chamber (152) to a second pressure. The second pressure is less than 100 torr. Once again, at or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (1912), the method shown in plot (1900) includes introducing a sterilant into sterilization chamber (152). The sterilant may be the same or different than the sterilant introduced in step (1906). At step (1914), the method shown in plot (1900) includes maintaining the second pressure in sterilization chamber (152) for a second period of time. The second period of time may be shorter or longer than the first period of time.

At step (1916), the method shown in plot (1900) includes applying a vacuum to sterilization chamber (152) to reduce the pressure within sterilization chamber (152) to a third pressure. The third pressure is less than 100 torr. For example, vacuum may be applied to sterilization chamber (152) to reduce the pressure to approximately 0 torr to approximately 5 torr.

At step (1918), the method shown in plot (1900) includes venting sterilization chamber (152) to increase the pressure within sterilization chamber (152) to a fourth pressure. The fourth pressure is greater than the third pressure but is still less than 100 torr. For example, in some instances the fourth pressure may be approximately 5 torr to approximately 30 torr greater than the third pressure, and in some instances the fourth pressure may be between approximately 10 torr to approximately 30 torr greater than the third pressure. At step (1920), the method shown in plot (1900) includes maintaining the fourth pressure in sterilization chamber (152) for a third period of time. The third period of time may be shorter or longer than any one of the first or second periods of time.

At step (1922), the method shown in plot (1900) includes applying a vacuum to sterilization chamber (152) to reduce the pressure within sterilization chamber (152) to a fifth pressure. The fifth pressure is less than 100 torr. For example, vacuum may be applied to sterilization chamber (152) to reduce the pressure to approximately 0 torr to approximately 5 torr. At step (1924), the method shown in plot (1900) includes introducing a sterilant into sterilization chamber (152). The sterilant may be the same or different than the sterilant introduced in step (1906) or step (1912). At step (1926), the method shown in plot (1900) includes maintaining the fifth pressure in sterilization chamber (152) for a fourth period of time. The fourth period of time may be shorter or longer than any one of the first, second, or third periods of time.

At step (1928), the method shown in plot (1900) includes applying a vacuum to sterilization chamber (152) to reduce the pressure within sterilization chamber (152) to a sixth pressure. The sixth pressure is less than 100 torr. For example, vacuum may be applied to sterilization chamber (152) to reduce the pressure to approximately 0 torr to approximately 5 torr. The sixth pressure is less than the fifth pressure.

At step (1930), the method shown in plot (1900) includes venting sterilization chamber (152) to increase the pressure within sterilization chamber (152) to a seventh pressure. The seventh pressure may be less than 100 torr. For example, in some instances the seventh pressure may be approximately 5 torr to approximately 30 torr greater than the sixth pressure, and in some instances the seventh pressure may be between approximately 10 torr to approximately 30 torr greater than the sixth pressure. At step (1932), the method shown in plot (1900) includes maintaining the seventh pressure in sterilization chamber (152) for a fifth period of time. The fifth period of time may be shorter or longer than any one of the first, second, third, or fourth periods of time. In some versions, one or more of steps (1908, 1914, 1920, 1926, 1932) may have a duration ranging from approximately 30 seconds to approximately 300 seconds.

At step (1934), the method shown in plot (1900) includes venting sterilization chamber (152) to increase the pressure within sterilization chamber (152) to an eighth pressure, shown as atmospheric pressure (ATM). While not shown, in some instances the eighth pressure may be approximately 5 torr to approximately 30 torr greater than the seventh pressure, and in some instances the eighth pressure may be between approximately 10 torr to approximately 15 torr greater than the seventh pressure. While not shown, prior to reaching atmospheric pressure (ATM), additional venting and maintaining steps similar to steps (1930, 1932) may be performed and in some instances may be repeated (e.g., once, twice, or three or more times).

While method steps (1902, 1904, 1906, 1908, 1910, 1912, 1914, 1916, 1918, 1920, 1922, 1924, 1926, 1928, 1930, 1932, 1934, 1936, 1934) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (1900), in the middle of the method shown in plot (1900), and after completing the method shown in plot (1900). For example, variations may include one or more steps before or after vacuum steps (1904, 1910, 1916, 1922, 1928) or one or more steps before or after venting steps (1918, 1930, 1934).

P. Fifteenth Exemplary Alternative Sterilization Cycle

Figure 20:
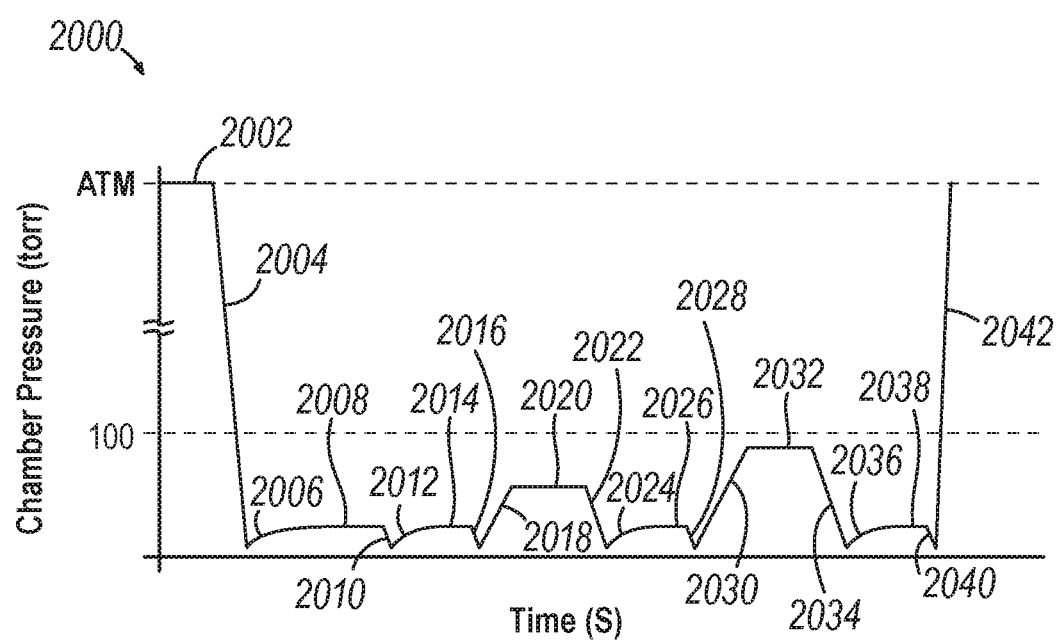
FIG. 20 depicts a graph showing a sixteenth exemplary plot of the pressure in a sterilization chamber of the sterilizing cabinet of FIG. 1 over time during performance of a fifteenth exemplary alternative sterilization cycle.

FIG. 20 depicts a graph showing a sixteenth exemplary plot (2000) of the pressure in sterilization chamber (152) of sterilizing cabinet (150) of FIG. 1 over time during performance of a fifteenth exemplary sterilization cycle. As described above, the sterilization cycle method associated with FIG. 20 may be performed on an endoscope or any other kind of article.

At step (2002), the method shown in plot (2000) includes receiving the endoscope in sterilization chamber (152). At step (2004), the method shown in plot (2000) includes applying a vacuum to sterilization chamber (152) to reduce the pressure within sterilization chamber (152) to a first pressure. It is desirable that the first pressure is less than 100 torr. At or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (2006), the method shown in plot (2000) includes introducing a sterilant into sterilization chamber (152). At step (2008), the method shown in plot (2000) includes maintaining the first pressure in sterilization chamber (152) for a first period of time. The second pressure may be greater than or less than the first pressure.

At step (2010), the method shown in plot (2000) includes applying a vacuum to sterilization chamber (152) to reduce the pressure within sterilization chamber (152) to a second pressure. The second pressure is less than 100 torr. Once again, at or below 100 torr, condensation is prevented without the need to either heat sterilization chamber (152) or the gas that introduced during the venting step(s). For example, vacuum may be applied to sterilization chamber (152) to reduce the pressure to approximately 0 torr to approximately 5 torr. At step (2012), the method shown in plot (2000) includes introducing a sterilant into sterilization chamber (152). The sterilant may be the same or different than the sterilant introduced in step (2006). At step (2014), the method shown in plot (2000) includes maintaining the second pressure in sterilization chamber (152) for a second period of time. The second period of time may be shorter or longer than the first period of time.

At step (2016), the method shown in plot (2000) includes applying a vacuum to sterilization chamber (152) to reduce the pressure within sterilization chamber (152) to a third pressure. For example, vacuum may be applied to sterilization chamber (152) to reduce the pressure to approximately 0 torr to approximately 5 torr. The third pressure may be greater than or less than the first or second pressure.

At step (2018), the method shown in plot (2000) includes venting sterilization chamber (152) to increase the pressure within sterilization chamber (152) to a fourth pressure. The fourth pressure is greater than the third pressure but is still less than 100 torr. For example, in some instances the fourth pressure may be approximately 5 torr to approximately 30 torr greater than the third pressure, and in some instances the fourth pressure may be between approximately 10 torr to approximately 15 torr greater than the third pressure. At step (2020), the method shown in plot (2000) includes maintaining the fourth pressure in sterilization chamber (152) for a third period of time. The fourth period of time may be shorter or longer than any one of the first, second or third periods of time.

At step (2022), the method shown in plot (2000) includes applying a vacuum to sterilization chamber (152) to reduce the pressure within sterilization chamber (152) to a fifth pressure. For example, vacuum may be applied to sterilization chamber (152) to reduce the pressure to approximately 0 torr to approximately 5 torr. As shown, the fifth pressure is less than the fourth pressure. The fifth pressure may be less than the first, second, or third pressures. At step (2024), the method shown in plot (2000) includes introducing additional sterilant into sterilization chamber (152). The sterilant may be the same or different to the sterilant introduced in step (2006) or step (2012). At step (2026), the method shown in plot (2000) includes maintaining the fifth pressure in sterilization chamber (152) for a fourth period of time. The fourth period of time may be shorter or longer than any one of the first, second, or third periods of time.

At step (2028), the method shown in plot (2000) includes applying a vacuum to sterilization chamber (152) to reduce the pressure within sterilization chamber (152) to a sixth pressure. The sixth pressure is less than 100 torr. For example, vacuum may be applied to sterilization chamber (152) to reduce the pressure to approximately 0 torr to approximately 5 torr.

At step (2030), the method shown in plot (2000) includes venting sterilization chamber (152) to increase the pressure within sterilization chamber (152) to a seventh pressure. The seventh pressure is greater than the sixth pressure. As shown, the seventh pressure is also greater than any one of the first, second, third, fourth, fifth, or sixth pressures. The seventh pressure may be less than 100 torr. At step (2032), the method shown in plot (2000) includes maintaining the seventh pressure in sterilization chamber (152) for a fifth period of time. The fifth period of time may be shorter or longer than any one of the first, second, third, or fourth periods of time.

At step (2034), the method shown in plot (2000) includes applying a vacuum to sterilization chamber (152) to reduce the pressure within sterilization chamber (152) to an eighth pressure. The eighth pressure is less than 100 torr. For example, vacuum may be applied to sterilization chamber (152) to reduce the pressure to approximately 0 torr to approximately 5 torr. At step (2036), the method shown in plot (2000) includes introducing a sterilant into sterilization chamber (152). The sterilant may be the same or different to the sterilant introduced in step (2006), step (2012), or step (2024). At step (2038), the method shown in plot (2000) includes maintaining the eighth pressure in sterilization chamber (152) for a sixth period of time. The sixth period of time may be shorter or longer than any one of the first, second, third, fourth or fifth periods of time. In some versions, one or more of steps (2008, 2014, 2020, 2026, 2032, 2038) may have a duration ranging from approximately 30 seconds to approximately 300 seconds.

At step (2040), the method shown in plot (2000) includes applying a vacuum to sterilization chamber (152) to reduce the pressure within sterilization chamber (152) to a ninth pressure. The ninth pressure is less than 100 torr. For example, vacuum may be applied to sterilization chamber (152) to reduce the pressure to approximately 0 torr to approximately 5 torr.

At step (2042), the method shown in plot (2000) includes venting sterilization chamber (152) to increase the pressure within sterilization chamber (152) to a tenth pressure, shown as atmospheric pressure (ATM). While not shown, in some instances the tenth pressure may be approximately 5 torr to approximately 30 torr greater than the ninth pressure, and in some instances the tenth pressure may be between approximately 10 torr to approximately 15 torr greater than the ninth pressure. While not shown, prior to reaching atmospheric pressure (ATM), additional venting and maintaining steps similar to steps (2030, 2032) may be performed and in some instances may be repeated (e.g., once, twice, or three or more times).

While method steps (2002, 2004, 2006, 2008, 2010, 2012, 2014, 2016, 2018, 2020, 2022, 2024, 2026, 2028, 2030, 2032, 2034, 2036) are shown in numerically increasing sequential order with each prior step terminating into the beginning of the next successive step, variations are also envisioned. Pulses may create agitation in sterilization chamber (154) causing convective mass transfer and speeding up the diffusion of the sterilant (e.g., hydrogen peroxide) into a lumen of the medical device (e.g., an endoscope). Conversely, introducing air into sterilization chamber (154) may cause more resistance to diffusion of sterilization into the lumen. Additional steps may be added before the method shown in plot (2000), in the middle of the method shown in plot (2000), and after completing the method shown in plot (2000). For example, variations may include one or more steps before or after vacuum steps (2004, 2010, 2016, 2022, 2028, 2034, 2040) or one or more steps before or after venting steps (1210, 1214, 1224).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of sterilizing an article, the method comprising: (a) receiving the article in a sterilization chamber; (b) applying a vacuum to the sterilization chamber to reduce pressure within the sterilization chamber to a first pressure, wherein the first pressure is less than 100 torr; (c) introducing a sterilant into the sterilization chamber; (d) maintaining the first pressure in the sterilization chamber for a first period of time; (e) venting the sterilization chamber to increase the pressure within the sterilization chamber to a second pressure, wherein the second pressure is greater than the first pressure but is still less than 100 torr; (f) maintaining the second pressure in the sterilization chamber for a second period of time; (g) venting the sterilization chamber to increase the pressure within the sterilization chamber to a third pressure; (h) maintaining the third pressure in the sterilization chamber for a third period of time; and (i) venting the sterilization chamber to increase the pressure within the sterilization chamber to atmospheric pressure, wherein the method further comprises, between at least one of steps (d) and (e), (f) and (g), or (h) and (i): (A) applying a vacuum to the sterilization chamber to reduce pressure within the sterilization chamber to a fourth pressure that is less than 100 torr, (B) introducing additional sterilant into the sterilization chamber, and (C) maintaining the pressure in the sterilization chamber for a fourth period of time.

Example 2

The method of Example 1, further comprising repeating sub-steps (A) through (C) between at least one of steps (d) and (e), (f) and (g), or (h) and (i).

Example 3

The method any one or more of Examples 1 through 2, wherein sub-steps (A) through (C) are performed between steps (d) and (e).

Example 4

The method any one or more of Examples 1 through 3, wherein sub-steps (A) through (C) are performed between steps (f) and (g).

Example 5

The method any one or more of Examples 1 through 4, wherein sub-steps (A) through (C) are performed between steps (h) and (i).

Example 6

The method of any one or more of Examples 1 through 2, wherein sub-steps (A) through (C) are performed between steps (d) and (e) and between steps (f) and (g).

Example 7

The method of Example 1, wherein sub-steps (A) through (C) are performed between steps (d) and (e), between steps (f) and (g), and between steps (h) and (i).

Example 8

The method of any one or more of Examples 1 through 7, further comprising repeating steps (g) and (h) at least once.

Example 9

The method of any one or more of Examples 1 through 8, further comprising applying a plasma to the sterilization chamber between steps (b) and (c).

Example 10

The method of any one or more of Examples 1 through 9, further comprising applying a vacuum, and after applying the vacuum introducing additional sterilant into the sterilization chamber during at least one of steps (e), (g), or (i).

Example 11

The method of any one or more of Examples 1 through 10, wherein the first, second, third, and fourth pressures are each below 100 torr.

Example 12

A method of sterilizing an article, the method comprising: (a) receiving the article in a sterilization chamber; (b) applying a vacuum to the sterilization chamber to reduce pressure within the sterilization chamber to a first pressure, wherein the first pressure is less than 100 torr; (c) introducing a sterilant into the sterilization chamber; (d) maintaining the first pressure in the sterilization chamber for a first period of time; (e) venting the sterilization chamber to increase the pressure within the sterilization chamber to a second pressure, wherein the second pressure is greater than the first pressure but is still less than 100 torr; (f) maintaining the second pressure in the sterilization chamber for a second period of time; (g) venting the sterilization chamber to increase the pressure within the sterilization chamber to a third pressure; (h) maintaining the third pressure in the sterilization chamber for a third period of time; and (i) venting the sterilization chamber to increase the pressure within the sterilization chamber to atmospheric pressure, wherein the method further comprises, between at least one of steps (d) and (e), (f) and (g), or (h) and (i): (A) applying a vacuum to the sterilization chamber to reduce the pressure within the sterilization chamber to a fourth pressure that is less than 100 torr, (B) introducing additional sterilant into the sterilization chamber, (C) maintaining the fourth pressure in the sterilization chamber for a fourth period of time, and (D) applying a vacuum to the sterilization chamber to reduce the pressure within the sterilization chamber to a fifth pressure that is less than 100 torr.

Example 13

The method of Example 12, further comprising repeating sub-steps (A) through (D) between at least one of steps (d) and (e), (f) and (g), or (h) and (i).

Example 14

The method of any one or more of Examples 12 through 13, wherein sub-steps (A) through (D) are performed between steps (d) and (e).

Example 15

The method of any one or more of Examples 12 through 14, wherein sub-steps (A) through (D) are performed between steps (f) and (g).

Example 16

The method of any one or more of Examples 12 through 15, wherein sub-steps (A) through (D) are performed between steps (h) and (i).

Example 17

The method of any one or more of Examples 12 through 13, wherein sub-steps (A) through (D) are performed between steps (d) and (e) as well as between steps (f) and (g).

Example 18

The method of any one or more of Examples 12 through 13, wherein sub-steps (A) through (D) are performed between steps (d) and (e), between steps (f) and (g), and between steps (h) and (i).

Example 19

The method of any one or more of Examples 12 through 18, further comprising repeating steps (g) and (h) at least once.

Example 20

The method of any one or more of Examples 12 through 19, further comprising applying a plasma to the sterilization chamber between steps (b) and (c).

Example 21

The method of any one or more of Examples 12 through 20, wherein the first, second, third, fourth, and fifth pressures are each below 100 torr.

Example 22

A method of sterilizing an endoscope, the method comprising: (a) receiving the endoscope in a sterilization chamber; (b) applying a vacuum to the sterilization chamber to reduce pressure within the sterilization chamber to a first pressure, wherein the first pressure is less than 10 torr; (c) introducing a sterilant into the sterilization chamber without either heating the sterilant or heating the sterilization chamber prior to introducing the sterilant into the sterilization chamber; (d) maintaining the first pressure in the sterilization chamber for a first period of time; (e) venting the sterilization chamber to increase the pressure within the sterilization chamber to a second pressure, wherein the second pressure is greater than the first pressure but is still less than 30 torr; and (f) applying a vacuum or venting to atmospheric pressure then applying the vacuum.

V. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of sterilizing an article, the method comprising:
   (a) receiving the article in a sterilization chamber;
   (b) applying a vacuum to the sterilization chamber to reduce pressure within the sterilization chamber to a first pressure, wherein the first pressure is less than 100 torr;
   (c) introducing a sterilant into the sterilization chamber;
   (d) maintaining the first pressure in the sterilization chamber for a first period of time;
   (e) venting the sterilization chamber to increase the pressure within the sterilization chamber to a second pressure, wherein the second pressure is greater than the first pressure but is still less than 100 torr;
   maintaining the second pressure in the sterilization chamber for a second period of time;
   (g) venting the sterilization chamber to increase the pressure within the sterilization chamber to a third pressure;
   (h) maintaining the third pressure in the sterilization chamber for a third period of time; and
   (i) venting the sterilization chamber to increase the pressure within the sterilization chamber to atmospheric pressure,
   wherein the method further comprises, between at least one of steps (d) and (e) or between steps (f) and (g):
   (A) applying a vacuum to the sterilization chamber to reduce pressure within the sterilization chamber to a fourth pressure that is less than 100 torr,
   (B) introducing additional sterilant into the sterilization chamber, and
   (C) maintaining the fourth pressure in the sterilization chamber for a fourth period of time.

2. The method of claim 1, further comprising repeating sub-steps (A) through (C) between at least one of steps (d) and (e) or between steps (f) and (g).

3. The method of claim 1, wherein sub-steps (A) through (C) are performed between steps (d) and (e).

4. The method of claim 1, further comprising performing sub-steps (A) through (C) between steps (f) and (g).

5. The method of claim 1, wherein sub-steps (A) through (C) are performed between steps (h) and (i).

6. The method of claim 1, wherein sub-steps (A) through (C) are performed between steps (d) and (e) and between steps (f) and (g).

7. The method of claim 1, wherein sub-steps (A) through (C) are performed between steps (d) and (e), between steps (f) and (g), and between steps (h) and (i).

8. The method of claim 1, further comprising repeating steps (g) and (h) at least once.

9. The method of claim 1, further comprising applying a plasma to the sterilization chamber between steps (b) and (c).

10. The method of claim 1, wherein the first, second, third, and fourth pressures are each below 100 torr.

11. A method of sterilizing an article, the method comprising:
  (a) receiving the article in a sterilization chamber;
  (b) applying a vacuum to the sterilization chamber to reduce pressure within the sterilization chamber to a first pressure, wherein the first pressure is less than 100 torr;
  (c) introducing a sterilant into the sterilization chamber;
  (d) maintaining the first pressure in the sterilization chamber for a first period of time;
  (e) venting the sterilization chamber to increase the pressure within the sterilization chamber to a second pressure, wherein the second pressure is greater than the first pressure but is still less than 100 torr;
  maintaining the second pressure in the sterilization chamber for a second period of time;
  (g) venting the sterilization chamber to increase the pressure within the sterilization chamber to a third pressure;
  (h) maintaining the third pressure in the sterilization chamber for a third period of time; and
  (i) venting the sterilization chamber to increase the pressure within the sterilization chamber to atmospheric pressure,
  wherein the method further comprises, between at least one of steps (d) and (e) or between steps (f) and (g):
    (A) applying a vacuum to the sterilization chamber to reduce the pressure within the sterilization chamber to a fourth pressure that is less than 100 torr,
    (B) introducing additional sterilant into the sterilization chamber,
    (C) maintaining the fourth pressure in the sterilization chamber for a fourth period of time, and
    (D) applying a vacuum to the sterilization chamber to reduce the pressure within the sterilization chamber to a fifth pressure that is less than 100 torr.

12. The method of claim 11, further comprising repeating sub-steps (A) through (D) between at least one of steps (d) and (e) or between steps (f) and (g).

13. The method of claim 11, wherein sub-steps (A) through (D) are performed between steps (d) and (e).

14. The method of claim 11, wherein sub-steps (A) through (D) are performed between steps (f) and (g).

15. The method of claim 11, further comprising performing sub-steps (A) through (D) between steps (h) and (i).

16. The method of claim 11, wherein sub-steps (A) through (D) are performed between steps (d) and (e) as well as between steps (f) and (g).

17. The method of claim 11, wherein sub-steps (A) through (D) are performed between steps (d) and (e), between steps (f) and (g), and between steps (h) and (i).

18. The method of claim 11, further comprising repeating steps (g) and (h) at least once.

19. The method of claim 11, further comprising applying a plasma to the sterilization chamber between steps (b) and (c).

20. The method of claim 11, wherein the first, second, third, fourth, and fifth pressures are each below 100 torr.

21. A method of sterilizing an endoscope, the method comprising:
  (a) receiving the endoscope in a sterilization chamber;
  (b) applying a vacuum to the sterilization chamber to reduce pressure within the sterilization chamber to a first pressure, wherein the first pressure is less than 10 torr;
  (c) introducing a sterilant into the sterilization chamber without either heating the sterilant or heating the sterilization chamber prior to introducing the sterilant into the sterilization chamber;
  (d) maintaining the first pressure in the sterilization chamber for a first period of time;
  (e) venting the sterilization chamber to atmosphere to increase the pressure within the sterilization chamber to a second pressure, wherein the second pressure is greater than the first pressure but is still less than 30 torr; and
  (f) applying a vacuum or venting to atmospheric pressure then applying the vacuum.

* * * * *